(12) United States Patent
Juhasz et al.

(10) Patent No.: US 11,864,899 B2
(45) Date of Patent: Jan. 9, 2024

(54) INTERACTIVE SKIN

(71) Applicants: Paul R. Juhasz, Houston, TX (US); Emily Tiernan, Houston, TX (US)

(72) Inventors: Paul R. Juhasz, Houston, TX (US); Emily Tiernan, Houston, TX (US)

(73) Assignee: INTERACTIVE SKIN, INC., Houston, TX (US)

( * ) Notice: Subject to any disclaimer, the term of this patent is extended or adjusted under 35 U.S.C. 154(b) by 156 days.

(21) Appl. No.: 16/387,394

(22) Filed: Apr. 17, 2019

(65) Prior Publication Data
US 2019/0320925 A1 Oct. 24, 2019

Related U.S. Application Data

(60) Provisional application No. 62/784,571, filed on Dec. 24, 2018, provisional application No. 62/659,586, filed on Apr. 18, 2018.

(51) Int. Cl.
*A61B 5/00* (2006.01)
*A61B 5/339* (2021.01)
*A61B 5/287* (2021.01)

(52) U.S. Cl.
CPC ............ *A61B 5/287* (2021.01); *A61B 5/0031* (2013.01); *A61B 5/339* (2021.01); *A61B 5/6804* (2013.01);
(Continued)

(58) Field of Classification Search
CPC ....... A61B 5/287; A61B 5/339; A61B 5/7445; A61B 5/746; A61B 5/0031; A61B 5/7405; A61B 5/6804; A61B 5/748
See application file for complete search history.

(56) References Cited

U.S. PATENT DOCUMENTS 10,080,950 B2  9/2018 Kelley
10,082,830 B2  9/2018 Lettow
(Continued)

OTHER PUBLICATIONS

Choi S, Lee H, Ghaffari R, Hyeon T, Kim DH. Recent Advances in Flexible and Stretchable Bio-Electronic Devices Integrated with Nanomaterials. Adv Mater. Jun. 2016;28(22):4203-18. doi: 10.1002/adma.201504150. Epub Jan. 18, 2016. PMID: 26779680. (Year: 2016).*

(Continued)

*Primary Examiner* — Gary Jackson
*Assistant Examiner* — Alexander M Eisenberg
(74) *Attorney, Agent, or Firm* — The Juhasz Law Firm

(57) ABSTRACT

Device and method for an interactive skin device for monitoring physical parameters of a body of a living thing. The interactive skin device may be positioned in or proximate to the skin of the living thing. The interactive skin device may monitor at least one physical parameter generated by an implanted medical device. The interactive device may include a flexible display layer, a cover layer, and a control circuit. The control circuit may be configured to control operation of the flexible display layer. The interactive skin device may trigger an alert when the at least one monitored physical parameter deviates from a predetermined threshold. The implanted medical device may be electrically connected to the interactive skin device by wireless, wired, optical, or combination electrical circuitry. In one embodiment, one or more ECG acquisition devices implanted into a human provide ECG data to an interactive skin device or external computing device.

25 Claims, 23 Drawing Sheets

(52) U.S. Cl.
CPC ............ *A61B 5/7405* (2013.01); *A61B 5/746* (2013.01); *A61B 5/748* (2013.01); *A61B 5/7445* (2013.01)

(56) References Cited

U.S. PATENT DOCUMENTS

| | | | |
|---|---|---|---|
| 10,379,576 B1 | 8/2019 | Lettow | |
| 2006/0079897 A1* | 4/2006 | Harrison | A61B 17/7055 63/900 |
| 2007/0032733 A1* | 2/2007 | Burton | A61B 5/7264 600/509 |
| 2007/0213629 A1* | 9/2007 | Greene | A61B 5/291 600/544 |
| 2008/0097559 A1* | 4/2008 | Eggers | A61B 18/14 607/102 |
| 2009/0275850 A1* | 11/2009 | Mehendale | A61B 5/35 600/509 |
| 2010/0036268 A1* | 2/2010 | Ferren | A61B 5/026 600/504 |
| 2010/0056873 A1* | 3/2010 | Allen | A61B 5/6804 600/300 |
| 2010/0081905 A1* | 4/2010 | Bommakanti | A61B 5/14532 600/347 |
| 2012/0078999 A1 | 3/2012 | Andrew et al. | |
| 2012/0165759 A1* | 6/2012 | Rogers | A61B 5/6867 606/228 |
| 2012/0204307 A1 | 8/2012 | De Mattei et al. | |
| 2013/0041235 A1* | 2/2013 | Rogers | H05K 1/0283 600/386 |
| 2013/0076649 A1 | 3/2013 | Myers et al. | |
| 2013/0096602 A1* | 4/2013 | Kumar | H01R 13/5219 606/191 |
| 2013/0332874 A1 | 12/2013 | Rosinko et al. | |
| 2014/0204035 A1 | 7/2014 | Chang | |
| 2014/0318699 A1 | 10/2014 | Longinotti-Buitoni et al. | |
| 2014/0373395 A1 | 12/2014 | White | |
| 2015/0062022 A1 | 3/2015 | Rabii | |
| 2015/0083615 A1 | 3/2015 | Lay et al. | |
| 2015/0164390 A1* | 6/2015 | Larvenz | A61B 5/6831 600/365 |
| 2015/0253930 A1 | 9/2015 | Kozloski et al. | |
| 2016/0041581 A1 | 2/2016 | Piccionelli et al. | |
| 2016/0066789 A1* | 3/2016 | Rogers | A61B 5/0031 604/20 |
| 2016/0174842 A1* | 6/2016 | Hyde | H01Q 21/30 342/52 |
| 2016/0188069 A1 | 6/2016 | Tao et al. | |
| 2016/0262670 A1* | 9/2016 | Wasson | A61B 5/0033 |
| 2016/0283101 A1 | 9/2016 | Schwesig et al. | |
| 2016/0327979 A1 | 11/2016 | Lettow | |
| 2016/0328043 A1* | 11/2016 | Moller | G06F 3/0416 |
| 2017/0000390 A1* | 1/2017 | Biederman | A61B 5/14532 |
| 2017/0027514 A1* | 2/2017 | Biederman | A61B 5/1451 |
| 2017/0052749 A1 | 2/2017 | Lee | |
| 2017/0090599 A1 | 3/2017 | Kuboyama et al. | |
| 2017/0365210 A1 | 12/2017 | Wang | |
| 2018/0280694 A1* | 10/2018 | Mashiach | A61N 1/3756 |
| 2018/0310360 A1 | 10/2018 | Lettow | |
| 2019/0030411 A1 | 1/2019 | Yang et al. | |

OTHER PUBLICATIONS

Office Action, U.S. Appl. No. 15/955,544, dated Jun. 9, 2020 (49 pages).
Office Action, U.S. Appl. No. 15/955,487, dated Feb. 19, 2020, 42 pages.
Research on flexible display at Ulsan National Inst. of Science and Technology (Ulsan, Korea), J. Park et al., npj Flexible Electronics 1, article No. 9 (Nov. 13, 2017), 46 pages.
Skinput: Appropriating the Body as an Input Surface, Harrison et al., Proceedings of CHI, Apr. 10-15, 2010, Atlanta, GA, 10 pages.
Skinput: Appropriating the skin as an Interactive Canvas, Harrison et al., Communications of the ACM, Aug. 2011, vol. 54, No. 8, pp. 111-118, Abstract only, 1 page.
Soft Pneumatics Actuator (SPA)—Skin, excerpt from Reconfigurable Robotics LAB RRL, Breadcrumb Navigator, Apr. 2018, 3 pages.
This 1mm sensor could monitor your body in real-time, Amelia Heathman, publ. in Wired Magazine, Aug. 4, 2016, 7 pages.
Engineered biomaterial could improve success of medical implants, Michelle Ma, publ in Univ. of Washington News, May 14, 2013, 5 pages.
5-Electrode array design and fabrication for implantable systems, P. Grabiec et al., Woodhead Publishing Series in Biomaterials, 2013, pp. 150-182, Abstract only, 2 pages.
Towards an implantable and refillable glucose sensor based on oxygen electrode principles, Sheng Luo Xie et al., publ in Sensors and Actuators B: Chemical, vol. 17, issue 2, Jan. 1994, pp. 133-142; Abstract only, 2 pages.
Wireless Implantable EMG sensing microsystem, Farnsworth et al., Conference Paper, Nov. 2008. Fig. 2-2, 4 pages.
Medical Implants—reliable implantable medical devices with glass bonding, Schott brochure, 2018, 3 pages.
Hermetic Implantable Packaging, Connectors for Medical Implant Industry, Pacaero Co., 2019, 3 pages.
Your implant could kill you, Jeanne Lenzer, New York Post, Dec. 16, 2017, 3 pages.
Drug-eluting medical implants, Zilberman et al., Handb. Exp. Pharmacol., 2010; (197) pp. 299-341; abstract only, 2 pages.
On the viability of implantable electrodes for the natural control of artificial limbs: Review and discussion, Ortiz-Catalan et al., Biomed Eng Online, 2012; 11: 33 Published on-line Jun. 20, 2012, 30 pages.
An Implantable Stimulator with Safety Sensors in Standard CMOS process for Active Books, Xiao Liu et al., IEEE Sensors Jour., vol. 16, issue 19, Oct. 1, 2016, 20 pages.
Implanted EEG Electrodes, from Epilepsy.com website, adapted from Blume H., The surgical treatment of epilepsy, in The comprehensive evaluation and treatment of epilepsy, eds. Schachter and Schomer, Academic press 1997, p. 197-206; adaptation publ Jan. 1, 2004, 3 pages.
Medical Device Standards and Implant Standards (listing), Amer. Soc. for Testing and Mtls. (ASTM), 2018, 31 pages.
Medical Implants Market by Type and by Materials—Global Opportunityh Analysis and Industry Forecast, 2014-2022, Deepa Katkare, Allied Market Research, 2018, 15 pages.

* cited by examiner

INTERACTIVE SKIN

This application claims priority to Prov. Appl. 62/659,586, filed on Apr. 18, 2018, and also claims priority to Prov. Appl. 62/784,571, filed on Dec. 24, 2018, both of which are hereby incorporated by reference in their entirety. Applicants cross-reference the following applications for information on Applicants' work with interactive skins: Interactive Skin for Vehicle, Ser. No. 15/955,544; and Interactive Skin for Wearable, Ser. No. 15/955,487; both filed Apr. 17, 2018.

BACKGROUND OF THE INVENTION

1. Field of the Invention

The present invention relates generally to body and implants, and more particularly, to body with interactive skin.

2. Description of the Related Art

The human body is made up of multiple systems that work together to form life. Body systems are an organized group of organs and tissue that forms a particular function. These functions work with other systems in the body. Some of the main systems of the body are digestive, circulatory, nervous, respiratory and muscular.

Organ systems include the Respiratory System (allows gas exchange between cells and the environment. Includes trachea and lungs); Digestive System/Excretory System (Ingests food and breaks it down into usable nutrients. Excretes solid waste products. Includes the mouth, esophagus, stomach, and intestines.); Cardiovascular/Circulatory System (Moves materials between body systems, including oxygen, nutrients, hormones, and waste products. Includes the heart, arteries, and veins.); Renal System/Urinary System (Cleans dissolved waste products from the blood and excretes them. Includes kidneys and bladder.); Endocrine System (Secrets chemical signals that allow body systems to act cooperatively as needed. Includes hormone-producing tissues of the pineal gland and pituitary gland in the brain; the thyroid gland; the adrenal glands; the pancreas; and the ovaries and testes.); Nervous System (Allows perception, emotion, thought, and rapid response to the environment. Includes brain and nerves.); Musculoskeletal system (Allows the body to move on command.); Integumentary System/Exocrine System (Covers the body and regulates its exchange with the outside world. Includes skin, hair, nails, sweat, and other glands which secrete substances onto the skin.); Lymphatic System/Immune System (Fights infection. Includes lymphatic vessels which permeate the body.); Reproductive System (Allows the production of offspring. Includes ovaries, uterus, mammary glands (breasts), penis, and testes.

Medical implants are devices or tissues that are placed inside or on the surface of the body. Many implants are prosthetics, intended to replace missing body parts. Other implants deliver medication, monitor body functions, or provide support to organs and tissues.

There is a need for improved monitoring and interaction with body and implants.

SUMMARY OF THE INVENTION

In one aspect, disclosed is an interactive skin device for monitoring physical parameters of a body of a living thing. The interactive skin device may be positioned in or proximate to the skin of the living thing. The interactive skin device may monitor at least one physical parameter generated by an implanted medical device. The interactive device may include a flexible display layer, a cover layer, and a control circuit. The control circuit may be configured to control operation of the flexible display layer. The interactive skin device may trigger an alert when the at least one monitored physical parameter deviates from a predetermined threshold.

In another aspect, an electrocardiographic data monitoring system may include one or more ECG acquisition devices implanted into a human. A processor may be configured to receive data from the at least one implanted ECG acquisition device. The processor may be configured to process the one or more ECG acquisition device data and to generate an output based on the processed data.

In another aspect, disclosed is a method for monitoring physical parameters of a living thing. The method may include positioning an interactive skin device in or proximate to the epidermis of the living thing; monitoring by the interactive skin device of at least one physical parameter generated by an implanted medical device; and triggering an alarm when the at least one monitored physical parameter deviates from a predetermined threshold.

The interactive skin may be used to support safety, communication connectivity within and without the body or at least one implant, and so on. The interactive skin may be used for displaying information and visual feedback to a user and for accepting input from a user.

Active portions of the interactive skin may be used to create virtual user interface controls such as buttons. During use, the buttons or other user input interface elements may be reconfigured. For instance, the user input interface elements may be repurposed for supporting user input operations in different operating modes of the interactive skin. Virtual buttons may be provided. They may be provided additional to or in place of tactile input/output components such as physical buttons and switches.

In operation, a virtual button may be a virtual volume button. The virtual button may control audio output volume. The virtual button may be repurposed based on user input. For example, the virtual button may be repurposed to become a virtual camera shutter button for taking a picture. As another example, the virtual button may be reconfigured to serve as a controller for another device function. Images displayed on the interactive skin may indicate to a user which function is currently being performed by the virtual button. Predetermined inputs to the touch-sensitive layer such as tapping, sliding, swiping, or other motions of an external object such as a finger across the interactive skin may be used to change the operating mode of the interactive skin.

DETAILED DESCRIPTION OF THE INVENTION

Figure 1:
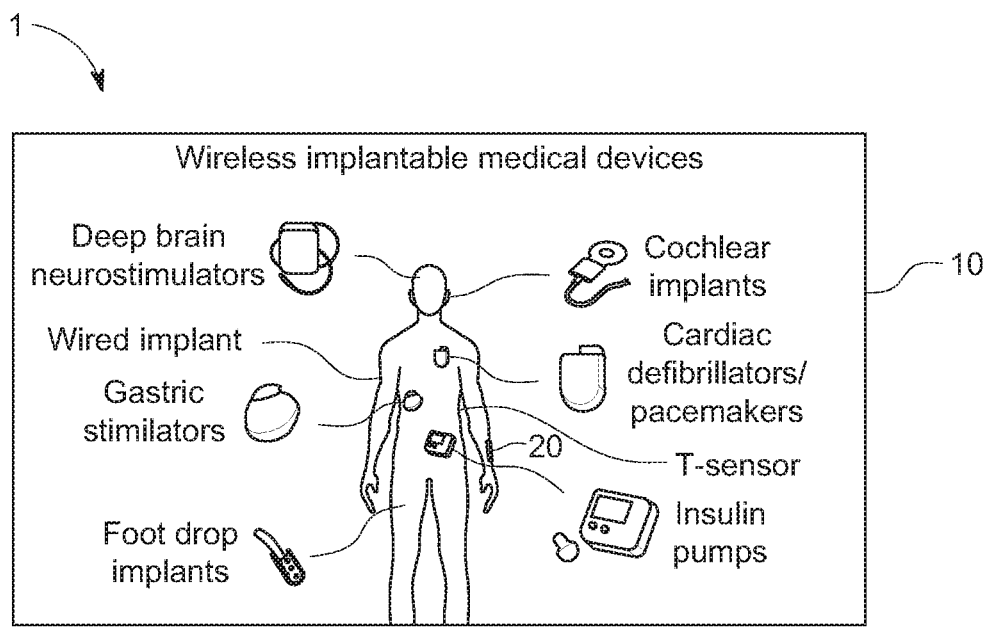
FIG. 1 depicts an illustrative embodiment of the present disclosure.
Figure 1:
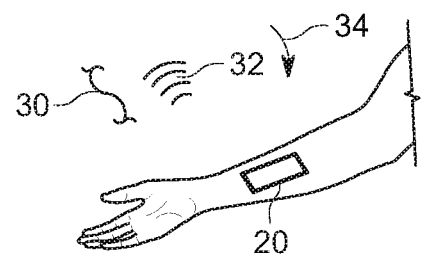

In the following detailed description, reference is made to the accompanying drawings that form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

As used herein, medical implants are devices or tissues that are placed inside or on the surface of the body. Implants may deliver medication, monitor body functions, or provide support to organs and tissues. Implants may be prosthetics, intended to replace missing body parts.

Disclosed is device and method for an interactive skin device for monitoring physical parameters of a body of a living thing. The interactive skin device may be positioned in or proximate to the skin of the living thing. The interactive skin device may monitor at least one physical parameter generated by an implanted medical device. The interactive device may include a flexible display layer, a cover layer, and a control circuit. The control circuit may be configured to control operation of the flexible display layer. The interactive skin device may trigger an alert when the at least one monitored physical parameter deviates from a predetermined threshold. The implanted medical device may be electrically connected to the interactive skin device by wireless, wired, optical, or combination electrical circuitry. In one embodiment, one or more ECG acquisition devices implanted into a human provide ECG data to an interactive skin device or an external computing device.

FIG. 1 depicts one or more implantable devices 10, at least one of which may be in electrical communication 34 with interactive skin 20 of this disclosure.

An implantable medical device for use with this disclosure may be an implantable medical device that once implanted may generate a signal indicative of a physical parameter of a body. Through wire, wireless, or optical connection of the implantable medical device to the interactive skin device 20, the interactive skin device 20 of this disclosure may monitor the signals generated by the implantable medical device that are indicative of a physical parameter of a body.

As depicted in FIG. 1, illustrative examples of an implantable medical device for use with this disclosure may include any of the depicted or other wireless, wired, or optical implantable medical devices configured with monitoring circuitry. Illustrative examples of wireless, wired, or optical implantable medical devices configured with monitoring circuitry may include a deep brain neurostimulator, a gastric stimulator, a foot drop implant, a cochlear implant, a cardiac defibrillator, a pacemaker, and an insulin pump. The implanted medical device may also include one or more wireless, wired, or optical implantable medical devices configured with monitoring circuitry such as monitoring circuitry configured orthopedic implants, cardiovascular implants, spinal implants, neurostimulators, ophthalmic implants dental implants, breast implants, facial implants, drug-eluting medical implants, The wireless, wired, or optical implantable medical devices configured with monitoring circuitry may be a monitoring circuitry configured drug-eluting medical implant, the drug-eluting medical implant selected from the group consisting of drug-eluting vascular stents, drug-eluting wound dressings and protein-eluting scaffolds for tissue regeneration.

The implantable medical devices depicted in FIG. 1 are implantable medical devices depicted for wireless communication of physical parameter data. Alternatively, the implantable medical devices may be wired, or optical implantable medical devices.

The physical parameter data monitored by the implantable medical device may include any physical parameter associated with the implantable medical device. In some illustrative examples, monitoring circuitry associated with the cardiac pacemaker may monitor the heart's rhythm; monitoring circuitry associated with a cochlear implant may monitor critical electric and neural activities in the implant; monitoring circuitry for smart stents may monitor in-stent restenosis; RFID, sensors and electric stimulators used in orthopedic implants may assess the functioning of an implanted orthopedic device and the surrounding tissue, as well as surgical recovery; and so on.

Figure 15A:
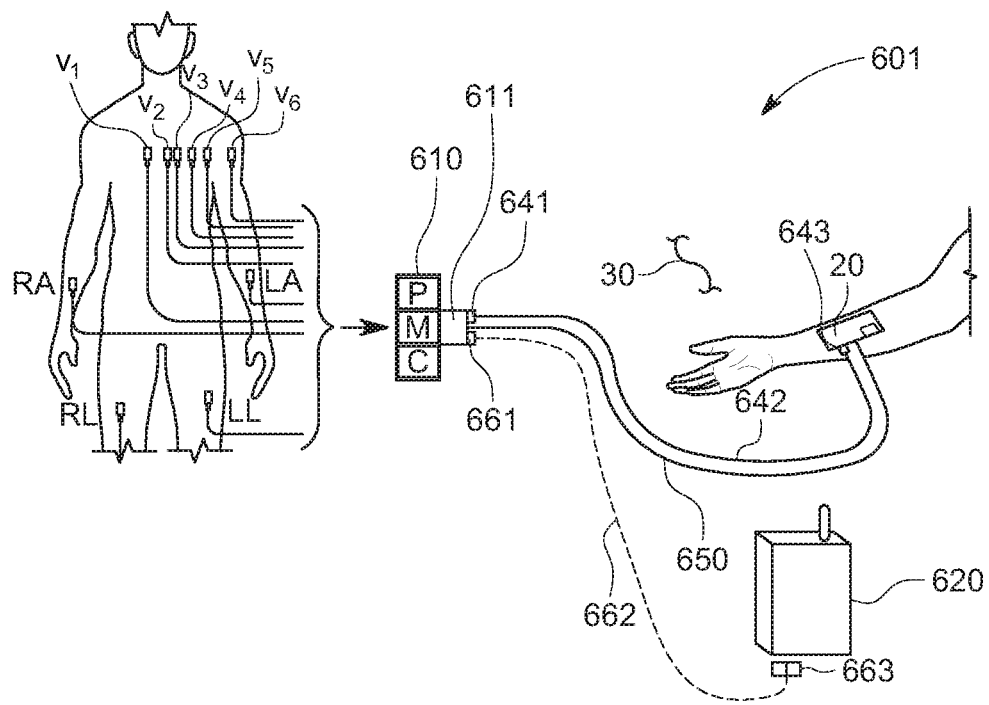
FIGS. 15A, 15B (collectively, FIG. 15) depict an illustrative embodiment of the present disclosure.
Figure 15B:
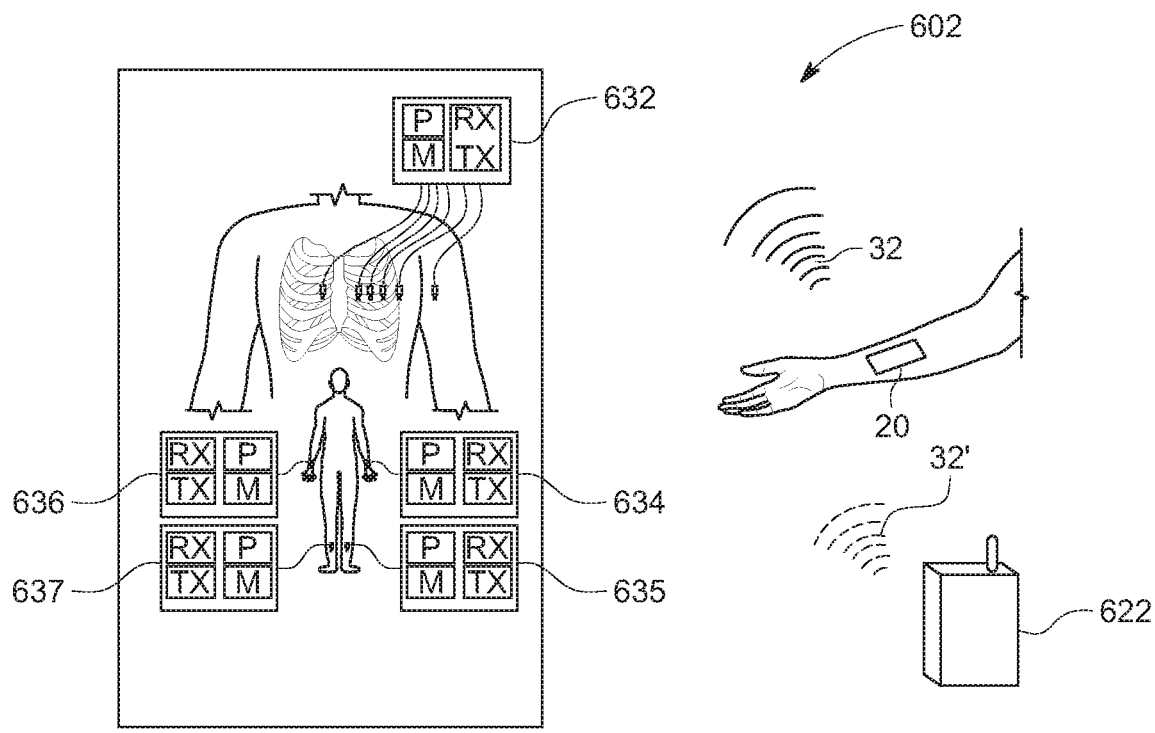

Communication between the implanted medical device and the interactive skin of this disclosure may be by wire, wireless, or optics. FIG. 1 illustrates an embodiment of this disclosure wherein the communication between the medical device and the interactive skin is wired 30 or wireless 32. FIG. 15 illustrates an embodiment of this disclosure wherein implanted ECG electrodes are in electrically communication with the interactive skin device 20 of this disclosure by wire 642, 650 (FIG. 15A) and wirelessly 32 (FIG. 15B). FIG. 15 also shows communication of implantable ECG electrodes with an external computing device, like smart phone 622, by wire 662 and wirelessly 32'.

FIG. 1 depicts the interactive skin device 20 of this disclosure may be positioned in or proximate to the skin of a living thing. In FIG. 1, the living thing may be a human. Alternatively, this disclosure may be used with any living thing, such as animals. FIG. 1 depicts the interactive skin device 20 positioned in or proximate to the skin of an arm of a human. In other illustrative embodiments, another or a plurality of parts of a body may be provided with an interactive skin of this disclosure. While FIG. 1 depicts the interactive skin device in a rectangular shape, it will be appreciated that the interactive skin device may have a circular, square, or any other shape that may be adapted to the body in accordance with the teachings of this disclosure. The size and shape and form factor of the interactive skin is a matter of design choice guided by the teachings of this disclosure.

Figure 2:
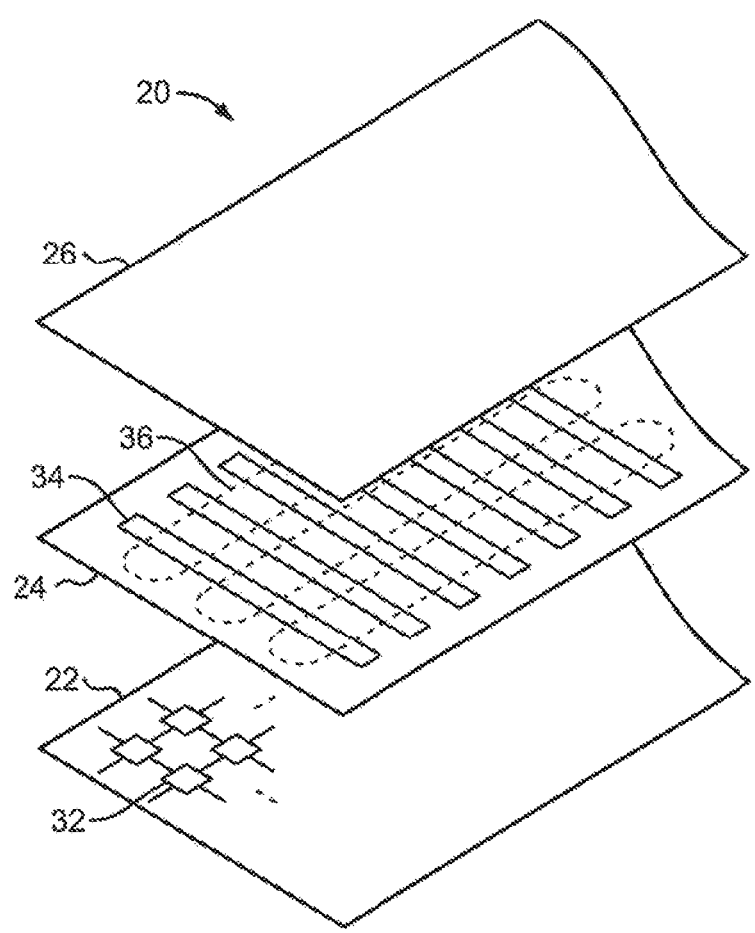
FIG. 2 depicts an illustrative embodiment of an interactive skin.

Turning to the interactive skin device, as depicted in FIG. 2, the interactive skin device may include a flexible display layer 22, a cover layer 26, and a control circuit (shown and explained in connection with FIG. 12A later in this disclosure).

More specifically, and as shown in FIG. 2, interactive skin 20 may be formed from multiple layers of material. The interactive skin 20 may be formed by stacking multiple layers.

In the illustrative embodiment, the interactive skin may include a flexible display layer 22, a touch sensitive layer 24, and a transparent display cover layer 26. The flexible display layer 22 may include a display pixel array 32 which may, for example, be an organic light-emitting diode (OLED) array. Other types of interactive skin pixel arrays may also be formed. For example, the image pixels may be formed from light-emitting diodes, plasma cells, electronic ink elements, liquid crystal display components, or other suitable image pixel structures compatible with the interactive skin. The flexible display layer may illustratively be formed using flexible sheets of polymer or other substrates having thicknesses of 10 microns to 0.5 mm or other suitable thicknesses.

The touch sensitive layer 24 may be a layer on which a pattern of indium tin oxide (ITO) electrodes or other suitable transparent electrodes have been deposited to form a capacitive touch sensor array. As depicted in FIG. 2, touch sensitive layer 24 may incorporate capacitive touch electrodes such as horizontal transparent electrodes 34 and vertical transparent electrodes 36. Touch sensitive layer may be configured to detect the location of one or more touches or near touches on touch sensitive later 24. Detection may be based on capacitive, resistive, optical, acoustic, inductive, or mechanical measurements, or any basis that can be measured with respect to the occurrence of one or more touches or near touches in proximity to the touch sensitive layer 24. The touch sensitive layer may illustratively be formed using flexible sheets of polymer or other substrates having thicknesses of 10 microns to 0.5 mm or other suitable thicknesses.

Software and/or hardware may be used to process the measurements to the detected touches to identify and track the one or more touches or near touches. A gesture may occur by moving one or more fingers or other objects in a particular manner on touch sensitive layer 24. Examples of gestures include tapping, pressing, and rocking. It may also include scrubbing, twisting, and changing orientation. It may include pressing with varying pressure and the like at essentially the same time, contiguously, or consecutively. A gesture may illustratively be characterized by a pinching, sliding, swiping, rotating, flexing, dragging, or tapping motion between or with any other finger or fingers. A single gesture may be performed in a variety of ways. For instance, with one or more hands, by one or more users, or any combination thereof.

In addition to flexible display layer 22 and touch sensitive layer 24, interactive skin 20 may include one or more structural layers. For example, interactive skin 20 may include the transparent display cover layer 26. In other words, flexible display layer 22 and touch sensitive layer 24 may be covered with a flexible or rigid cover layer. The transparent display cover layer 26 may be formed from a glass or plastic and may be flexible but alternatively may be rigid. The transparent layer may be configured to hermetically seal, environmentally protect, and so on, the flexible layers lying under the transparent layer.

In addition, flexible display layer 22 and touch sensitive layer 24 may include one or more structural layers. Flexible display layer 22 and touch sensitive layer 24 may be mounted on a support structure. For example, they may be mounted on a rigid support. Layers of adhesive may be used in attaching interactive skin layers to each other and may be used in mounting interactive skin layers to rigid and flexible structural layers. The structural layer may be a body to which the interactive skin is attached.

Alternatively, interactive skin may be integrated with a material configured to provide more structure to the interactive skin. For instance, the interactive skin may integrated into injection-molded plastics. In this embodiment, the integrated structure may provide both interactive skin and support structure.

The interactive skin may be designed with materials and with an operation that meets guidelines that make a medical device safe for use with a body in the manner described herein. For instance, the implanted interactive skin device discussed in FIG. 2 and associated circuitry may include an encapsulation layer including a biocompatible material. The encapsulation layer may be configured to seal the interactive skin device so as to isolate inner components of the interactive skin device from the environment of the living thing.

The one or more biocompatible materials may include metallic biomaterials, ceramic biomaterials, polymers biomaterials, natural biomaterials, and glass.

As explained, the interactive skin device may include a touch sensitive layer 24 and control circuit (explained in FIG. 12A) may be configured to control operation of touch sensitive elements. The cover layer may include a transparent display cover layer 26.

The interactive skin may provide data on the at least one monitored physical parameter of the implanted medical device. The interactive skin may provide data on the at least one monitored physical parameter on touch input of the interactive skin device. The interactive skin may receive and display data from outside the body, such as from an external computing device, like a smart phone or an external computing device in a network.

As explained in greater detail in the illustrative embodiment depicted in FIGS. 3-11, there are many ways in which the interactive skin device may be attached to the body.

FIG. 3 depicts the proximate positioning of the interactive skin device may be below the epidermis of the living thing, in this example, the ventral side of the lower arm of a human. In FIGS. 3A-C, the interactive skin device 20 is depicted below the epidermis, and indeed below the skin and more particularly between skin 110 and muscle 106 of the body (FIG. 3C).

Alternatively, the interactive skin device may be positioned within the skin. For example, as depicted in FIGS. 3D-3F the interactive skin device may be positioned in between the epidermis layer 107 of cells and the dermis layer 108 of cells that are included in a skin. In another embodiment, the interactive skin may be positioned within the skin so as have some portion lie partly below the epidermis with the remaining portion of the interactive skin lying in the epidermis layer.

In other embodiments, the interactive skin device may be positioned to lie partly above the epidermis with remaining portion positioned within the skin, either in the epidermis layer, the dermis layer, or both.

In other embodiments, the interactive skin device may be positioned to lie partly above the epidermis with a part of the remaining portion positioned partly within the skin, and the remaining part of the remaining portion positioned below the skin.

Any configuration of the interactive skin device in relation to the skin or the parts of the skin; that is to say at least some part or all of the interactive skin being above the skin, in the skin, in the epidermis layer of the skin, in the dermis layer of the skin, below the skin, and so on are within the teachings of this disclosure.

In the embodiment depicted in FIG. 3, the interactive skin device may be surgically attached to the body. As depicted in FIG. 3A, an incision may be made in the skin 110 in the shape of the interactive skin device 20 of this disclosure and the skin 110 peeled back. Fatty tissue 106 underneath the skin and above muscle 105 may be removed to form a recess 112 for receiving the interactive skin device 20. The folded back skin 110 may be returned to cover the recess 112 and the interactive skin device 20. The edges of the fold may then be stitched 114 to adjacent skin as shown to secure the interactive skin device to the body and close the opening to minimize infection. Additional epidermis from other regions of the body may be taken and used if more epidermis is needed to complete this operation.

In an alternative embodiment, the skin 110 peeled back may include some but not all layers of the skin. For instance, as depicted in FIGS. 3D, 3E, 3F, the epidermis layer 107 of the skin 110 may be peeled back to form the recess 112 for receiving the interactive skin device against the dermis layer 108 of the skin 110. The interactive skin 20 may be placed against the dermis layer 108 of the skin 110 and the peeled back epidermal layer 107 folded back over the interactive skin and stitched as previously explained; with additional skin as may be needed to enclose the interactive skin underneath the epidermis layer taken from another part of the body. This embodiment may minimize the risk of infection since there remaining portions of the skin between the interactive skin of this disclosure and the body may protect the body from the environment.

In an alternative embodiment, an upper region of the epidermis may be peeled back to create the recess for receiving the interactive skin.

The interactive skin device may trigger an alert when at least one monitored physical parameter deviates from a predetermined threshold. For instance, if a monitored physical parameter deviates from a normal value programmed into associated control circuitry, the interactive skin device may trigger an alert. More on alerts is disclosed elsewhere in this disclosure.

Figure 4A:
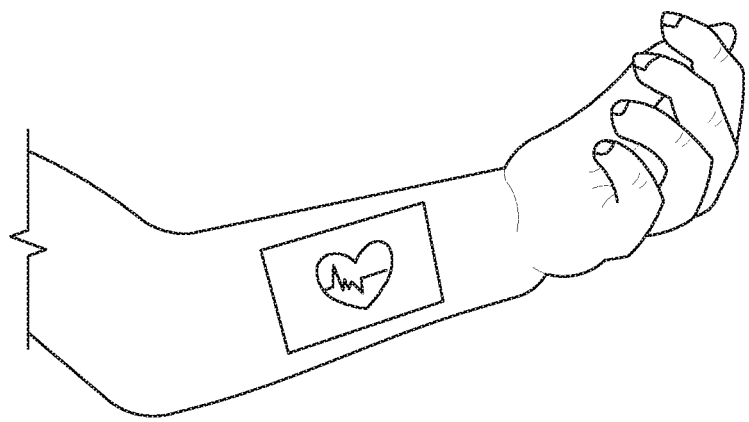
FIGS. 4A, 4B (collectively, FIG. 4) depict an illustrative embodiment of the present disclosure.

As depicted in FIG. 4, the visual display rendered on the flexible display layer 22 may be projected through the epidermis. FIG. 4A shows a rendering of an icon, in this example, in the shape of a heart with a heartbeat shown therein. Such a rendering may appear for example if monitoring of a parameter from an implanted pacemaker indicates the parameter deviates from a predetermined value. In this example, the interactive skin device generates an alert as a result of the deviation of the parameter from the predetermined value; and that alert is the display of the heart and heartbeat icon. The appearance of the icon may be an alert for the human to go see a doctor. As another example, the heart and heartbeat icon may also appear if the human is instrumented with the ECG electrodes explained in FIG. 15 and the interactive skin device detects data from one or more ECG electrodes that deviates from a predetermined value.

A different icon may be used to alert conditions with respect to different physical parameters. For instance, an alert from an instrumented orthopedic implant may be in the shape of a bone; an alert from an instrumented cochlear implant may be in the form factor of an ear, and so on.

The icons may be static or dynamic. For instance, a static icon may just display an icon which remains unchanged over time. A dynamic icon may be a displayed icon that changes over time. For instance, in the example with the heart and heartbeat icon, the heartbeat icon may simulate the heartbeat of the human. As another example, the display may render other data such as heart rate, blood pressure, other vitals, and so on.

The visual display may trigger on a condition, be rendered periodically, continually, on demand, any combination, and so on. The triggering and duration of a visual display is a matter of design choice based on system capabilities including energy availability guided by the teachings of this disclosure.

Figure 4B:
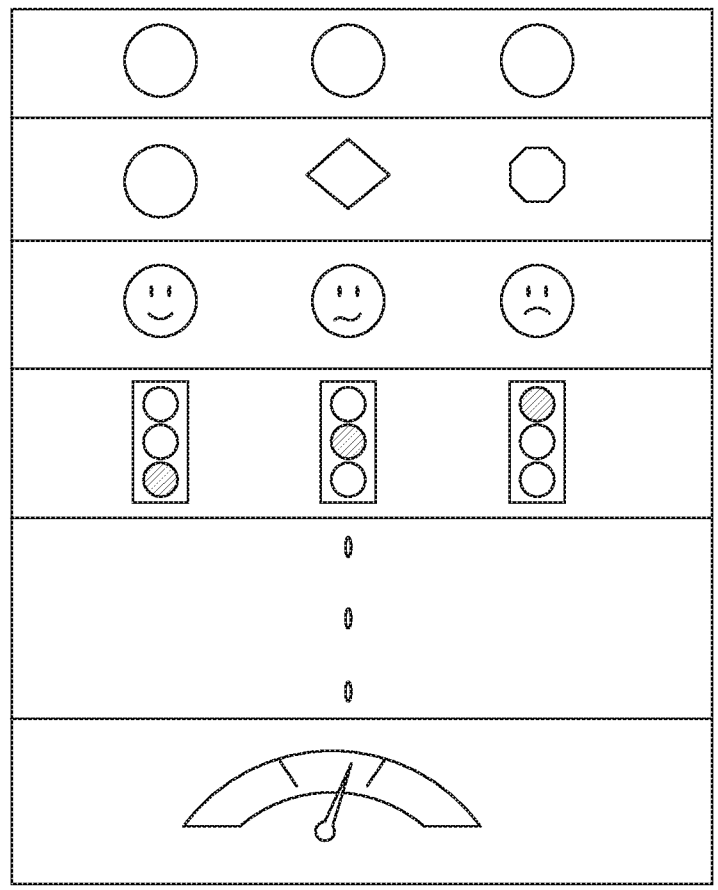

As shown in FIG. 4B, the alert may be one of a set of alerts with different alerts in the set alerting the human to different levels of action. For instance, the alerts depicted in the far left in FIG. 4B may appear if the data output reported by the interactive skin device is normal, the alerts depicted in the middle may be indicators that data is showing physical parameter data as perhaps creeping up towards danger or borderline, and the alerts depicted in the far right may be alerts of danger. The needle and gauge depicted in the bottom of FIG. 4B presents another icon that used may be used with this disclosure. The icon of the alert is a matter of design choice guided by the teachings of this disclosure.

The cover layer 26 may include at least one raised pattern that may be recognized through the epidermis from external to the body on touch. The at least one raised pattern may be associated with at least one function of the interactive skin device. Touch of the at least one raised pattern may activate the at least one function. For instance, a raised pattern of a single dot may be associated with power on, a raised pattern of two dots may be associated with display data, and so on. As another example, the raised patterns may be letters of the alphabet, of the Braille alphabet, Morse code alphabet, an alphabet created by design choice, symbols created by design choice, combinations of the foregoing, and so on. The raised pattern is a matter of design choice guided by the teachings of this disclosure.

While the alert discussed in the illustrative example is a visual display, the alert may be an auditory alert, or an audio-video combination. In these embodiments, the alerts pass through the epidermis of the body. As a result, they may provide a transdermal visual display and a transdermal audio display. Moreover, the visual display rendered on the flexible display layer may be projected through and rendered on the epidermis. As a result, the epidermis of the human may serve as the projector screen for viewing the images rendered on the display of the interactive skin device. Alternatively, the epidermis may serve as a screen filter for the display projected by the interactive skin device of this disclosure.

Figure 5A:
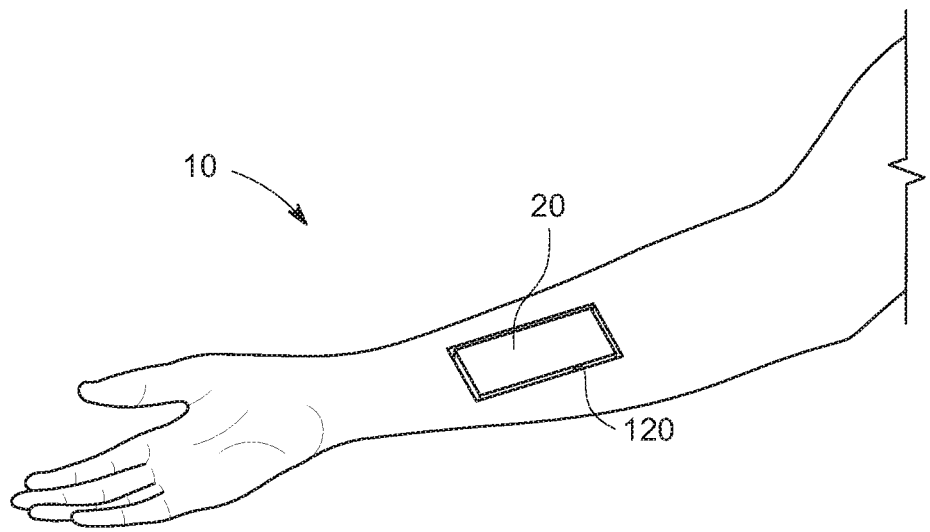
FIGS. 5A, 5B (collectively, FIG. 5) depict an illustrative embodiment of the present disclosure.
Figure 5B:
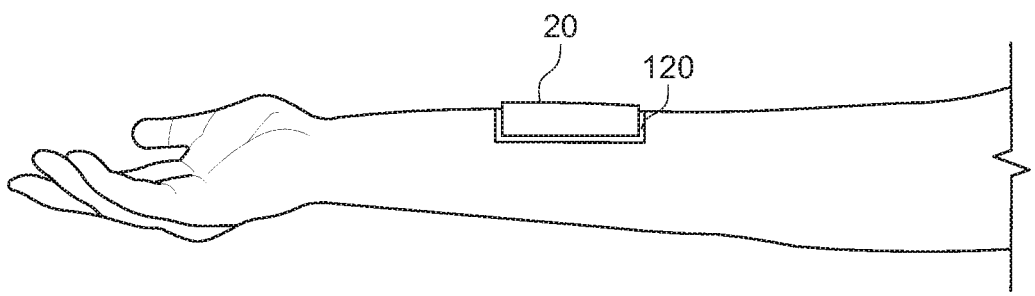

FIG. 5 depicts an illustrative embodiment wherein the interactive skin device 20 may include an interactive skin device supporting layer 120 disposed between the interactive skin device and the epidermis. The interactive skin device supporting layer may be an adhesive. The adhesive may be adapted to a portion of the epidermis. The adhesive may be an epidermal adhesive.

Figure 6A:
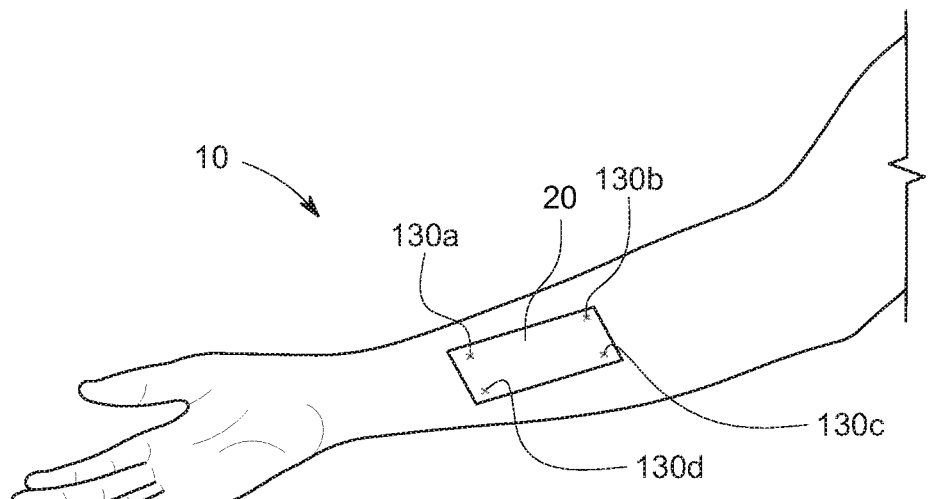
FIGS. 6A, 6B (collectively, FIG. 6) depict an illustrative embodiment of the present disclosure.
Figure 6B:
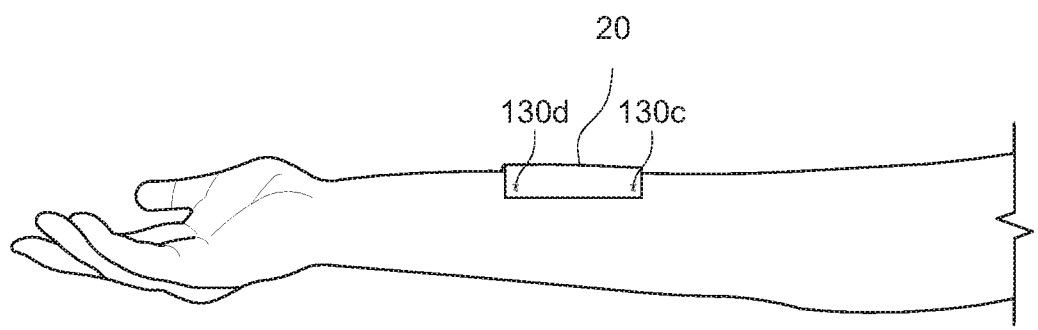

FIG. 6 depicts an illustrative embodiment wherein interactive skin device may include an interactive skin device supporting member configured to hold the interactive skin device 20 in a spatial relationship with respect to the epidermis. The interactive skin device supporting member may include one or more connectors 130*a-d* configured for attaching the interactive skin device to the human. The one or more connectors may include one or more adhesive spots 130*a-d* disposed on the epidermis configured for attaching the interactive skin device to the human when the interactive skin device is placed against the one or more adhesive spots.

Alternatively, the one or more connectors may be surgical stitches. The one or more connectors may be surgically attached to the body.

Figure 7A:
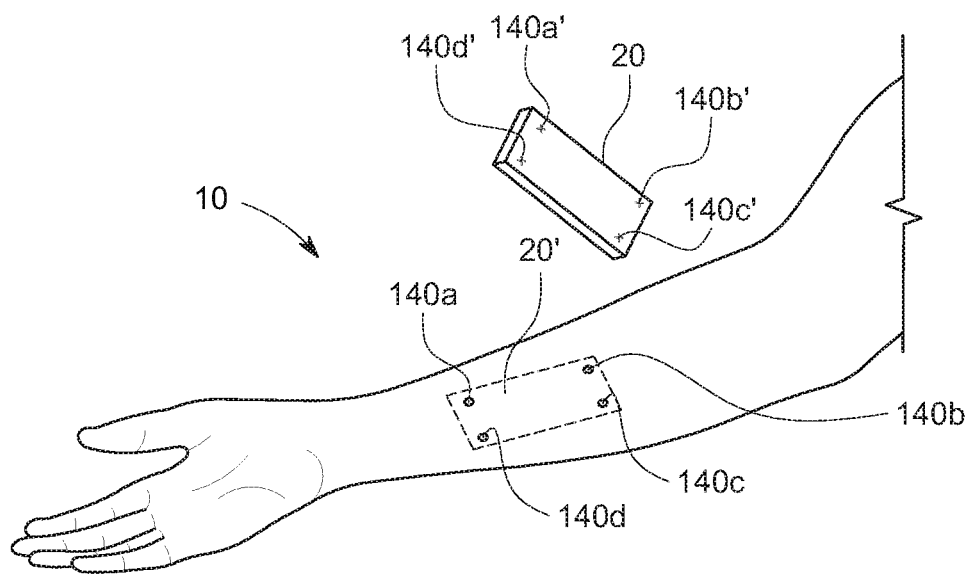
FIGS. 7A, 7B (collectively, FIG. 7) depict an illustrative embodiment of the present disclosure.
Figure 7B:
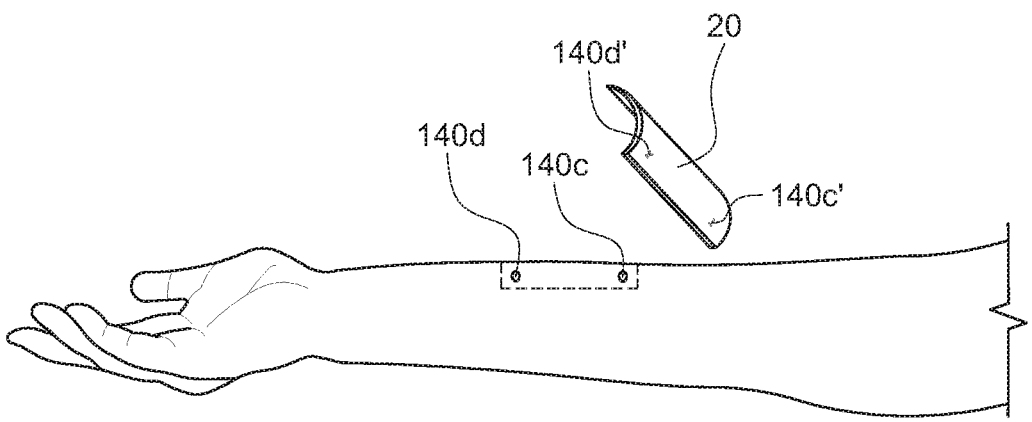

FIG. 7 depicts an illustrative embodiment wherein the one or more connectors may be one of a pair of a Velcro hook and loop fastener 140*a-d* surgically attached to the human, another of the pair of a Velcro hook and loop fastener and 140*a'-d'* being attached to the interactive skin device 20, such as by an adhesive, and the engagement of the one and the other of the pair of a Velcro hook and loop fastener being the attachment of the interactive skin device to the human.

Figure 8A:
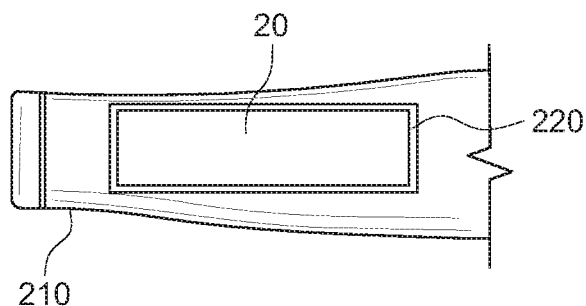
FIGS. 8A, 8B (collectively, FIG. 8) depict an illustrative embodiment of the present disclosure.
Figure 8B:
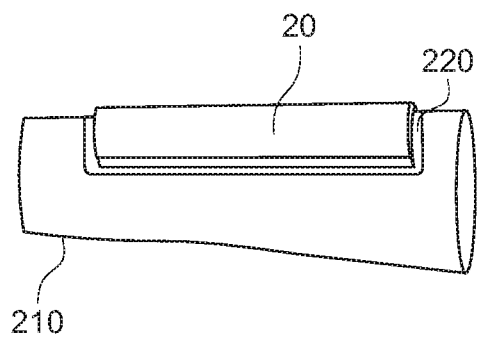
Figure 9A:
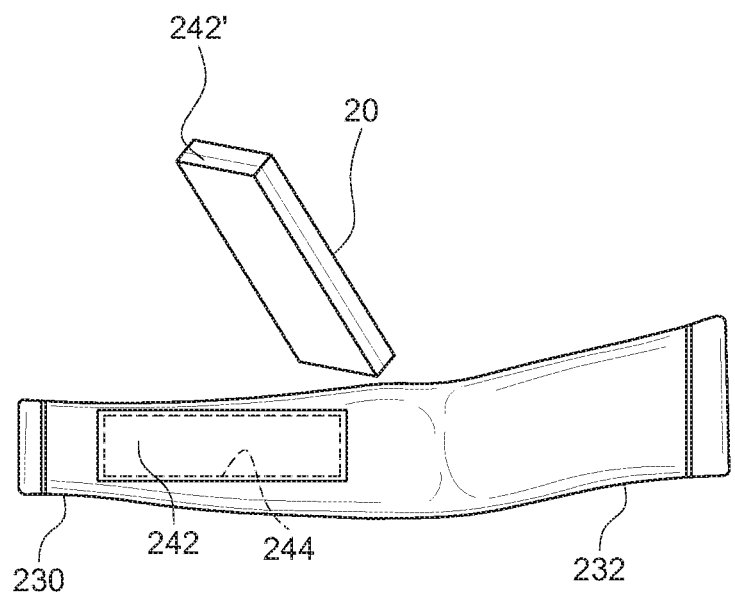
FIGS. 9A, 9B (collectively, FIG. 9) depict an illustrative embodiment of the present disclosure.
Figure 9B:
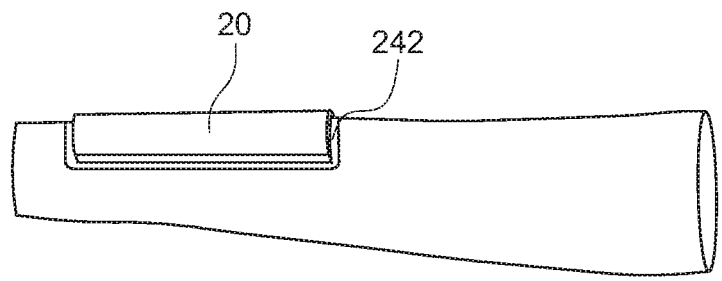

FIGS. 8 and 9 depict two embodiments wherein the proximate positioning of the interactive device may be outside the epidermis of the human.

FIG. 8 depicts an interactive skin device supporting layer 210 disposed between the interactive skin device 20 and the epidermis (not shown). As depicted, the interactive skin device supporting layer 210 may be a sleeve configured to be worn about a portion of the body of the human. The interactive skin device may be adapted to a portion of the sleeve.

The sleeve may be made from wearable material like nylon, cotton, spandex natural rubber, and so on. The sleeve may be made from a compressive material to fit tightly around the skin when worn. The sleeve may. include a biocompatible material. The interactive skin device may be adapted to a ventral portion of the sleeve and the sleeve may be disposed about a forearm of the human. Alternatively, the sleeve may be disposed about another part of the human such as a thigh, a waist, a chest, an upper arm, a neck, and so on.

The interactive skin device to sleeve supporting member may include one or more connectors configured for attaching the interactive skin device to the sleeve.

For example, as depicted in FIG. 8, interactive skin device 20 may be adapted to a supporting member configured to hold the interactive skin device in a spatial relationship to the sleeve. The interactive skin device supporting layer may be an adhesive 220. The adhesive may be adapted to a portion of the sleeve. The interactive skin device may be adapted to a portion of the adhesive.

As another example, as depicted in FIG. 9, the one or more connectors may be one of a pair of a Velcro hook and loop fastener 242 attached to the sleeve, such as by stitching 244, an adhesive, and so on. Another of the pair of a Velcro hook and loop fastener 242 may be attached to the interactive skin device, such as by an adhesive, and the engagement of the one and the other of the pair of a Velcro hook and loop fastener may be the attachment of the interactive skin device to the sleeve.

FIG. 9 depicts the interactive skin device adapted to a ventral portion of the sleeve and the sleeve may be disposed about at least a portion of a forearm and upper arm of the human. The interactive skin device may be adapted to a ventral portion of the sleeve and the sleeve may be disposed about a thigh of the human. The interactive skin device may be adapted to the dorsal or other portions of the sleeve. The interactive skin device adapted to the sleeve may be disposed about any body part of the human.

Figure 3A:
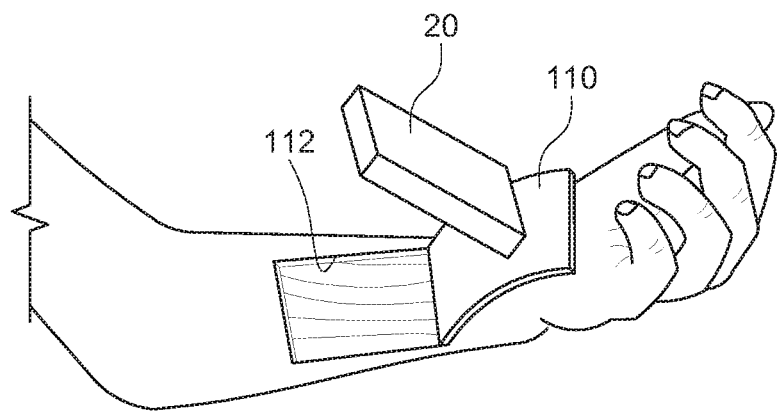
FIGS. 3A, 3B, 3C, 3D, 3E, 3F (collectively, FIG. 3) depict an illustrative embodiment of the present disclosure.
Figure 3B:
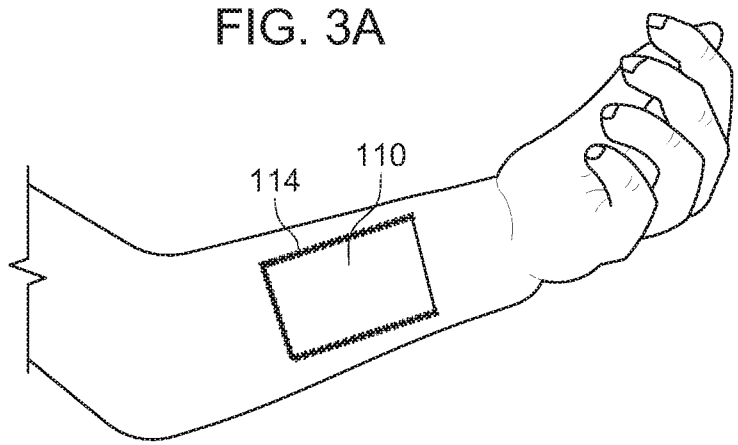
Figure 3C:
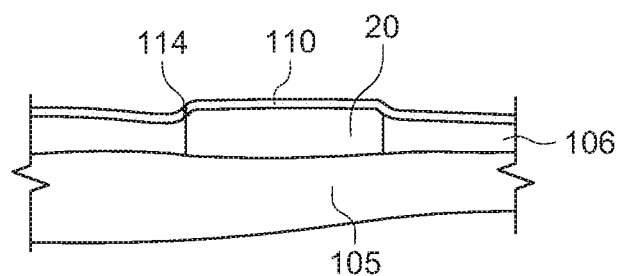
Figure 3D:
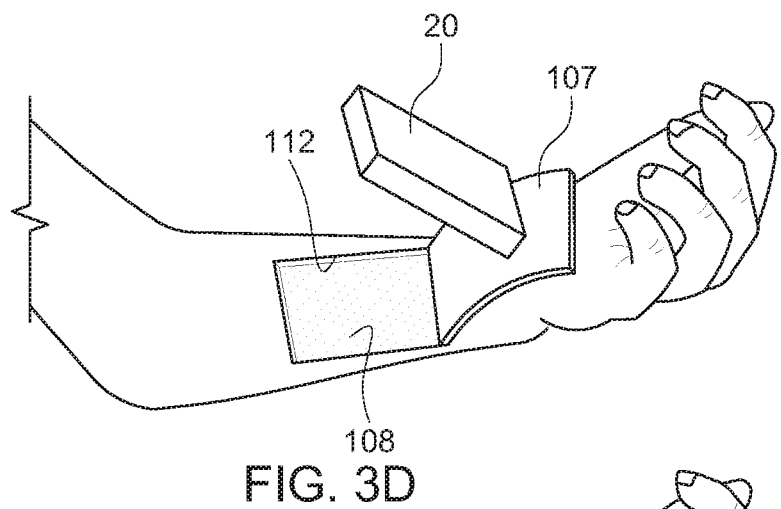
Figure 3E:
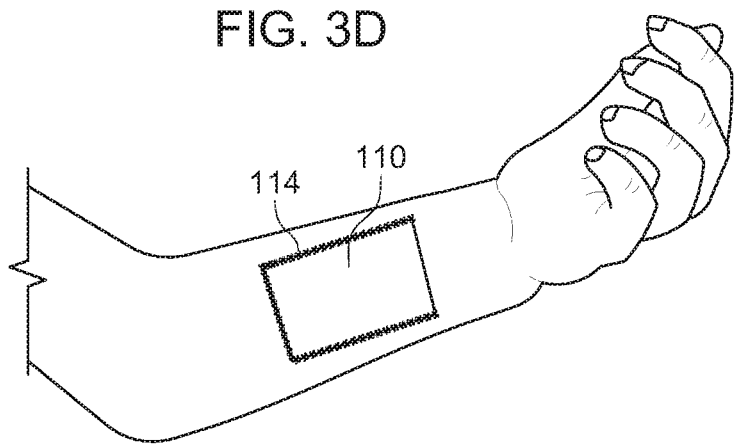
Figure 3F:
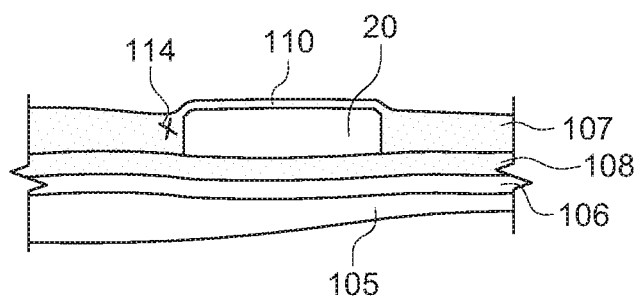
Figure 10A:
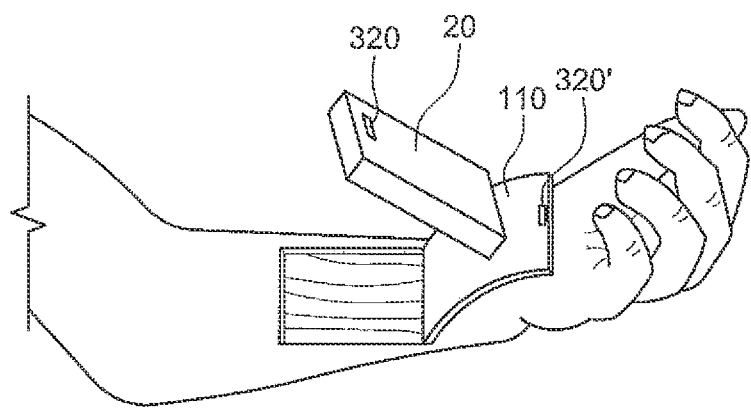
FIGS. 10A, 10B, 10C, 10D, 10E, 10F (collectively, FIG. 10) depict an illustrative embodiment of the present disclosure.
Figure 10B:
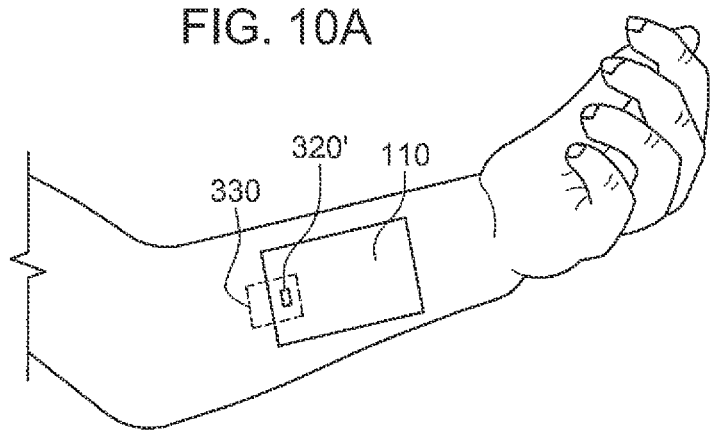
Figure 10C:
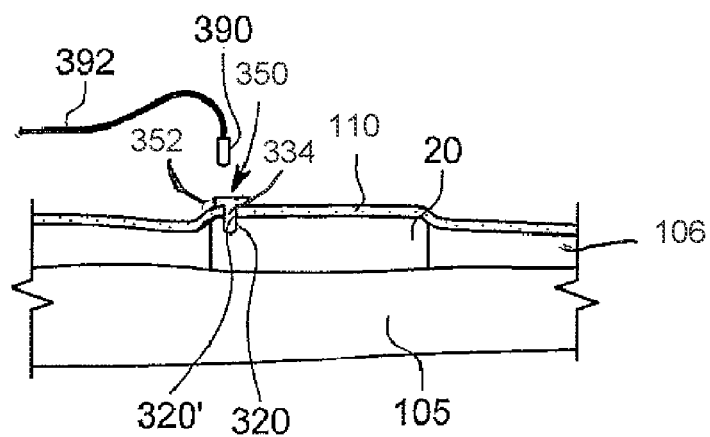
Figure 13:
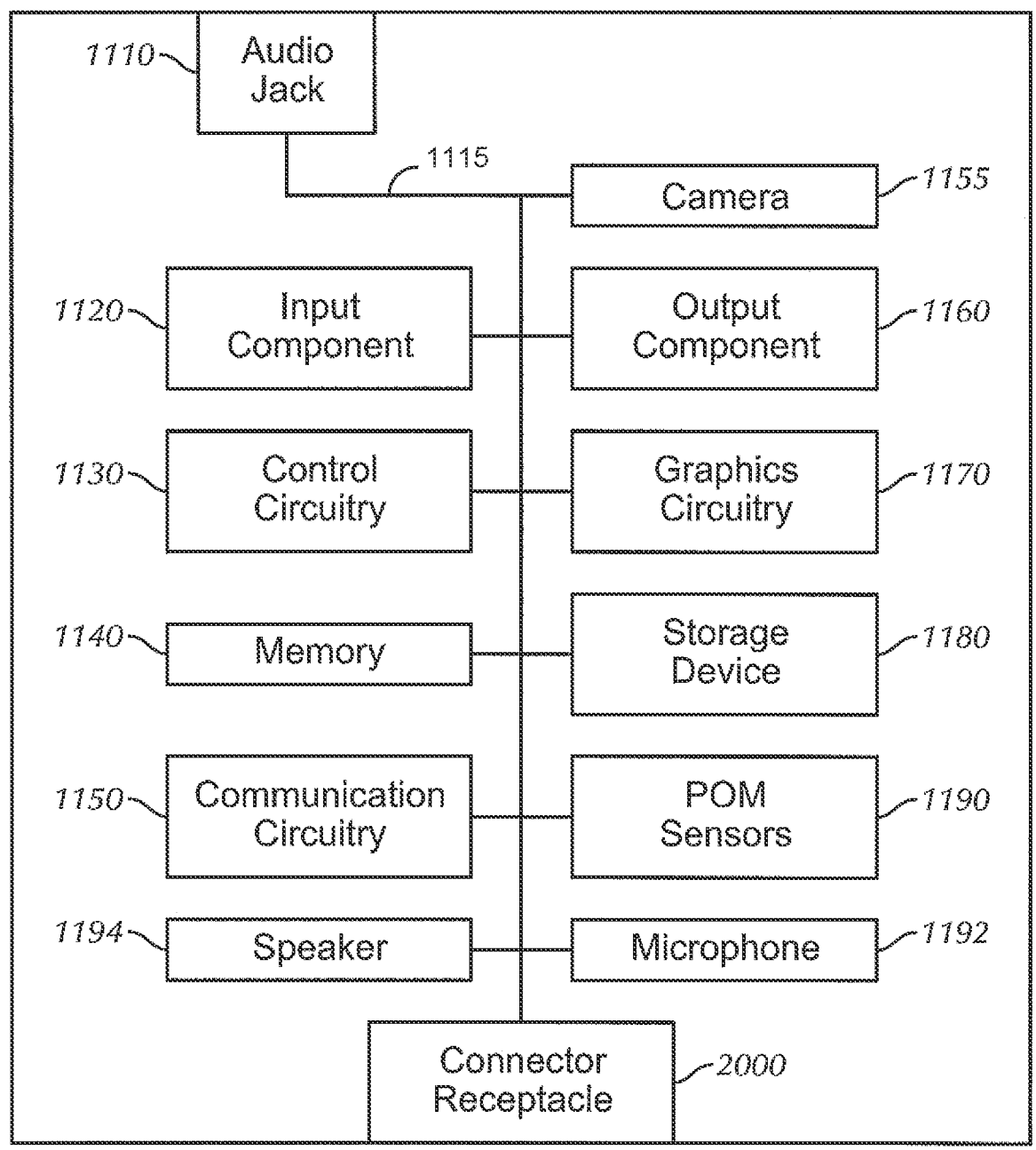
FIG. 13 depicts an illustrative embodiment of the present disclosure.

FIGS. 10A, 10B, 10C depict the interactive skin device adapted to the body as disclosed in FIGS. 3A, 3B, 3C further including a port 320 selected from the group consisting of an input port and an output port as explained in FIG. 13. The peeled back portion of skin 110 of the human may be provided with an opening 320' configured for enabling an electrical connection between an external connector 390 of a wire connector 392 and the port 320.

The interactive skin device may include a sealant layer 330. The sealant layer may be disposed across the port when the port is not being used. The sealant layer may be configured to seal the implanted interactive skin device so as to protect the human from infection from the opening in the epidermis.

Figure 10D:
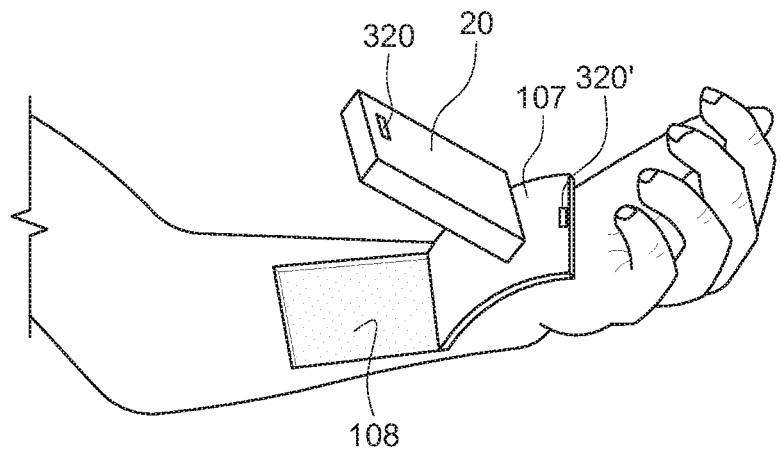
Figure 10E:
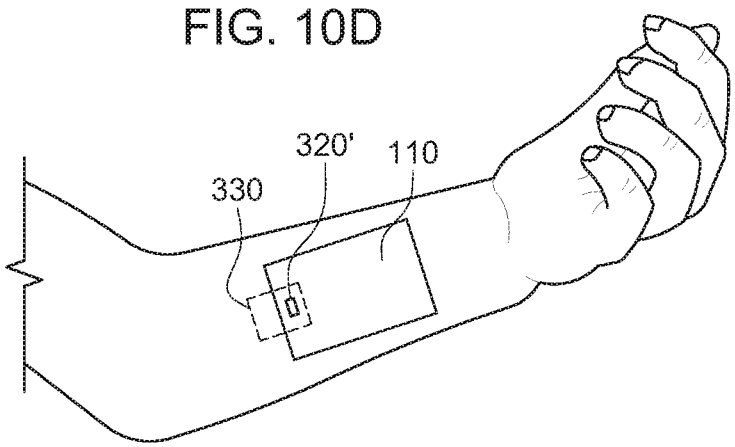
Figure 10F:
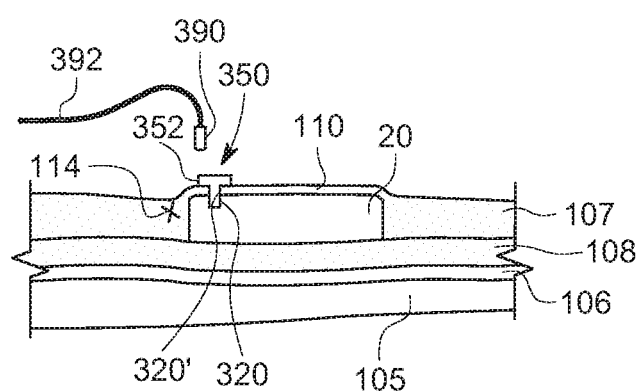

The sealant layer 330 of the implanted interactive skin device may be in the form factor of a sealant layer applied onto the epidermis over the opening. Alternatively, the sealant layer may be in the form factor of a sealant layer 331 as shown in FIG. 10B or a sealant plug 350 as shown in FIG. 10C wherein a protruding member 334 extends into opening 320' or also into port 320 and the stop 352 at the top of the sealant plug 350 seals opening 320' from the environment. The sealant plug may be configured to being disposed in the port defined in the implanted interactive skin device when the port is not being used. The sealant plug may protect the human from infection from the opening in the epidermis. Sealant layer is a matter of design choice guided by the teachings of this disclosure. FIGS. 10D, 10E, 10F depict the interactive skin device adapted to the body as disclosed in FIGS. 3D, 3E, 3F. Since the interactive skin device in this device lies inside of the skin (e.g., between epidermis 107 and dermis 108 in this example), there remains skin (e.g., dermis 108) between the interactive skin and the body which may protect the body from the environment against infection in which case the sealant layer 330, sealant plug 350, and so on may not be needed. But sealant layer 330, sealant plug 350, and so on may still be used to provide further protection of the body from the environment.

In either and other cases, an antiseptic may be applied to and around the opening 320' as needed to maintain the area free from infection. For instance, the sealant layer may be replaced as needed and the skin in that region may have applied to it an antiseptic before application of the sealant layer to the skin. Antiseptic treatment of the skin in the applicable region may also be used with the sealant plug and other embodiments of the sealant layer 330. An antiseptic procedure may also be periodically useful in embodiments where no sealant layer sealant plug, are used.

Figure 11A:
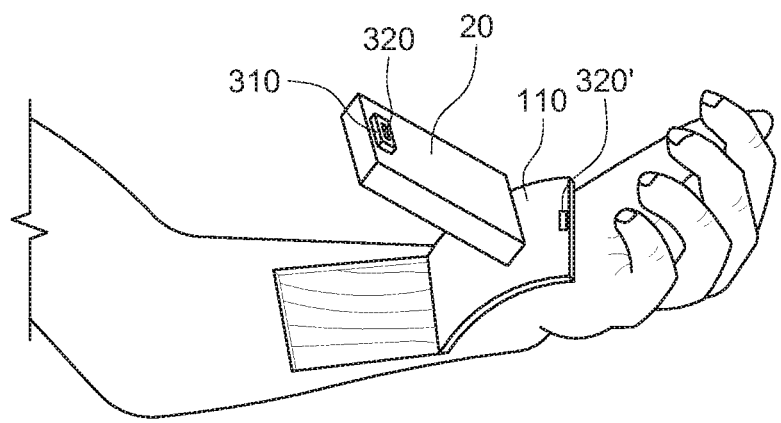
FIGS. 11A, 11B (collectively, FIG. 11) depict an illustrative embodiment of the present disclosure.
Figure 11B:
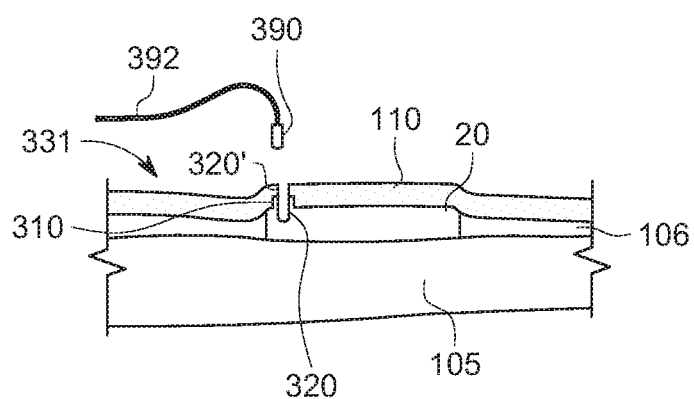

FIG. 11 depicts the interactive skin device of FIGS. 10A, 10C wherein the interactive skin device 20 may include a member 310 that extends away from the interactive skin device so as to extend into the epidermis when the interactive skin device is placed below the skin in this example. In this embodiment, the interactive skin device lies below the skin and the extension member 310 extends into the skin so that port 320 opens to opening 320' in a layer of the skin, such as the epidermis layer. This places the port 320 in the epidermis layer so that skin may heal around the port to better isolate the body from the environment against infection while allowing the port 320 to be accessed from outside the body.

As disclosed, openings in the skin of a body may be provided to allow a user to access the interactive skin of this disclosure. In another embodiment, the interactive skin of this disclosure lies underneath the skin of a body with a user providing inputs and receiving outputs to and from the interactive skin of this disclosure through the skin of the body. Where the cover layer for interactive skin 20 is flexible, input-output components that rely on the presence of flexible layers may be mounted at any suitable location under the interactive skin. For example, they may be mounted along peripheral portions of the interactive skin, in a central portion of the interactive skin, and so on. For example, a speaker component may be mounted, for example, to the interactive skin illustratively under, alongside of, or in proximity to the interactive skin. In another embodiment, input-output components may be remotely located and associated with the interactive skin.

Where the flexible layers are covered by a rigid cover glass layer or other rigid cover layer, one or more openings may be provided in the rigid layer and electronic components may be mounted for example, to the body under the openings of the interactive skin.

The openings in interactive skin and/or body may accommodate electronic components like volume, ringer, sleep, other buttons; openings for an audio jack, data port connectors, removable media slots; camera; sensors; microphone; speaker; and so on. With or without openings, FIG. 13 depicts illustrative electronic components that may be accommodated by interactive skin and/or implant. One or more components may be configured in a housing connected to or associated with the body. The one or more components may be distributed along or about the body or implant such as about the interactive skin. The one or more components may be distributed in an injection-molded plastic incorporating both interactive skin and support structure. The one or more components may be provided by a computing device like a smart phone or remote computing device.

The interactive skin 20 may bend into and run under or inside the body. For example, interactive skin 20 may extend along body, bend into the body, extend under a portion of the body and a portion of interactive skin 20 may be visible through an opening of the body.

Illustratively, a portion of interactive skin may be configured to include virtual buttons, virtual switches, scrolling displays, and so on. Alternatively, these features may be provided in other portions of interactive skin, like portion. The openings that may be created in the body may be round openings, rectilinear openings, oval shaped or oddly shaped openings, and so on.

Display portions of interactive skin 20 may be separated from other portions of interactive skin 20. This may illustratively be done by using a printed or painted mask on an internal surface of the cover layer. Alternatively, portions of the interactive skin may be separated by selectively activating and inactivating display pixels. This may create virtual borders, virtual sections, or other visual delineations between portions of interactive skin 20.

In some embodiments, portions of interactive skin 20 such as peripheral regions may be inactive. Other portions of interactive skin 20 such as a rectangular central portion may correspond to an active part of interactive skin 20. In the active region, an array of image pixels may be used to present text and images to a user of interactive skin 20. In the active region, interactive skin 20 may include touch sensitive components. These components may allow for input and interaction with a user of interactive skin 20. In an alternative embodiment, the active region may include sensors for detecting conditions as explained later in this disclosure.

In another illustrative embodiment, all or substantially all of the interactive skin 20 may be covered with display pixels. Edge portions of interactive skin 20 may contain portions of the array of image pixels for presenting to present text and images to a user of interactive skin 20. The edge portions may also include touch-sensitive components for input and interaction with a user of interactive skin 20.

Figure 12A:
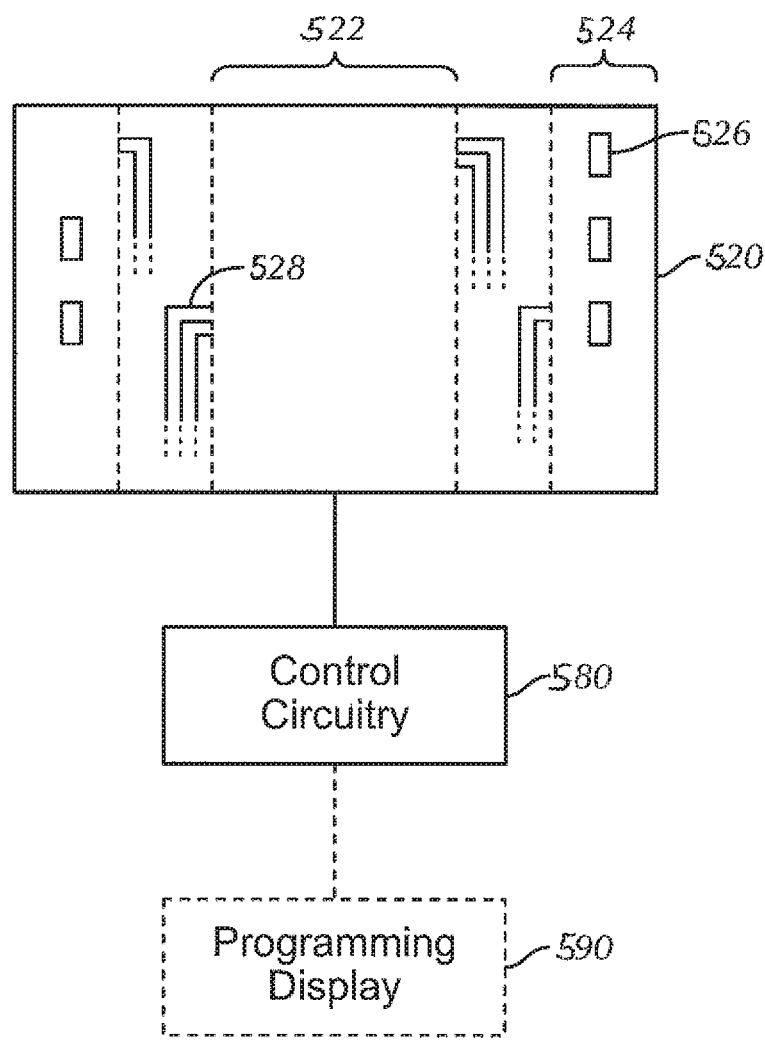
FIGS. 12A, 12B (collectively, FIG. 12) depict an illustrative embodiment of the present disclosure.

FIG. 12A shows how interactive skin 20 may be coupled to control circuitry such as control circuitry 580 associated with the interactive skin 20. The control circuitry may be dedicated to the interactive skin. Alternatively, a plurality of interactive skins according to this disclosure may have a dedicated controller. In another illustrative embodiment, a controller may be provided in a body and may be in electrical communication with the interactive skin and may control the functioning of the interactive skin. In another embodiment, the controller may be a smart phone that may be in electrical communication with the interactive skin of this disclosure.

Figure 12B:
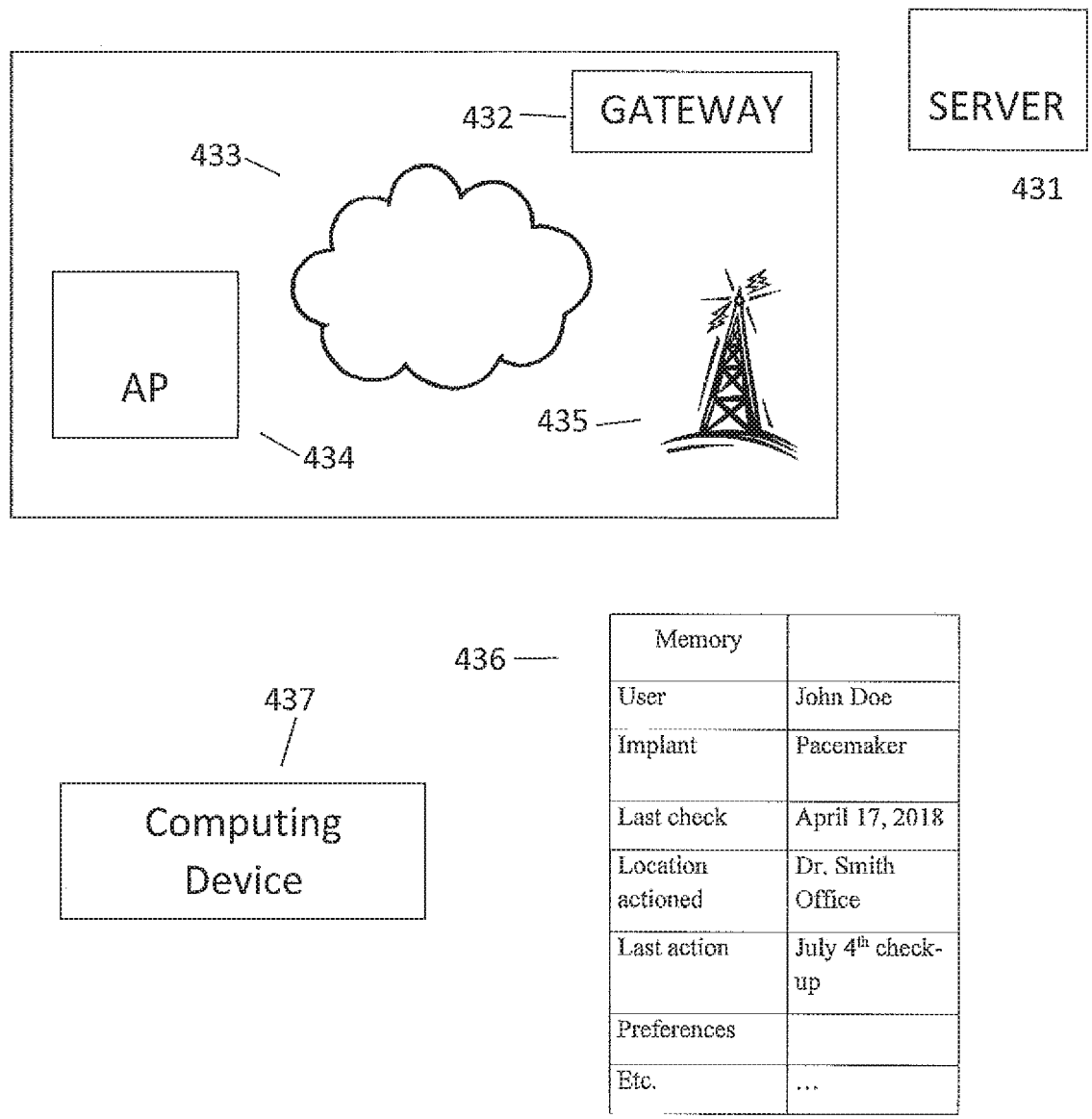

In another embodiment depicted in FIG. 12B, a controller may be a remote computing device such as computing device 437 or server 431 that may recognize and establish electrical communication with communication circuitry 1150 associated with an interactive skin of a body explained below. For example, computing device 437 in a doctor's office, restaurant, a store, a hotel, an office, a business establishment, a home, a building, or in any location, inside or outside, may establish an electrical communication with the body through the communication circuitry associated with the interactive skin.

Alternatively, server 431 may do the same, a communication link in that case may go through an access point 434 and across Internet 433. Communication may go through a base station 435 and over a cellular network if for example server 431 or communication circuitry associated with an interactive skin are configured to communicate in that way. Communication from server 431 may go through computing device 437, which may be a personal computer, a mobile terminal like a smart phone or other computer device. Alternatively, server 431 may communicate with communication circuitry associated with an interactive skin of through an Ethernet or other network connection.

In an illustrative embodiment, computing device 437 may be in a doctor's office, restaurant, an office, a home, or outside location and configured to recognize and establish an electrical communication with all implants in that location. The computing device may be configured to cause one or more implants associated with interactive skin within range to change some configuration. For instance, if a dangerous condition of operation of an implant or of a physical condition of the body (e.g. high temperature, high blood pressure, etc.), the computing device may provide instructions to the implant through this disclosure. In another embodiment, a condition of the body or implant may be displayed on the interactive skin and the user may monitor and may change configurations such as increasing dose of a chemical, etc.

The computing device or server 431 may also track information from sensors associated with the body and/or implant with interactive skin to track the location of the body and/or implant in a location. In this way the store may be able to collect data on the body and implant.

The user of the interactive skin may also communicate through communication circuitry 1150 with computing device 437 and server 431.

In combination, a body with interactive skin and a remote or other computing device may form a system for interacting with the body and/or implant with interactive skin of this disclosure.

The communication link may be established, by for example, an application running on computing device associated with the implant, including a control circuitry 580 as depicted as control circuitry 1130 in FIG. 12A and associated memory and communication circuitry.

The body with interactive skin of this disclosure may be configured to communicate with any computing device.

In another illustrative example, the information programmed into memory associated with the interactive skin may include the smart phone number of the smart phone of the user of the implant. After receiving information from the body and/or implant with interactive skin in the manner explained in this disclosure, the computing device may communication information to the user by sending information to the smart phone of the user, such as by texting the user.

Turning back to FIG. 12A, the communication link between controller and the interactive skin may be created by wire, wireless, or by optical communication. In wireless and optical embodiments, the interactive skin may be provided with communication circuitry such as wireless communication hardware and associated software to communicate wirelessly, such as by Wi-Fi, WAN, blue tooth or other wireless communication technology. This in order to allow a controller to control the interactive skin.

Control circuitry 580 may illustratively include memory storage. Examples of storage include flash memory, hard disk drive memory, and solid state storage devices. It also includes other nonvolatile memory, random-access memory and other volatile memory, and so on.

Control circuitry 580 may also include processing circuitry. The processing circuitry of control circuitry 580 may include microprocessors, digital signal processors, microcontrollers, application specific integrated circuits. It may also include power management unit (PMU) circuits, and processing circuitry that is part of other types of integrated circuits.

Control circuitry 580 controls and may be preprogrammed with instructions stored in a memory for execution by a processor in controlling the interactive skin, such as what content is displayed on the interactive skin. The control circuit also enables the interactive display to be controlled by a user. Illustratively, control is by user interaction with the interactive skin.

In one embodiment, the display rendered on interactive skin as previously explained provides a user interface for controlling the interactive skin. But as previously explained, interactive skin 20 may be controlled from within or without the body, such as by using a programming display 590 inside or outside the body to program the interactive skin. Communication between the controller and the interactive skin may be as previously explained.

Control circuitry 580 may be used to run software such as internet browsing applications and voice-over-internet-protocol (VOIP) telephone call applications. The control circuity may be used to run software such as email applications, media playback applications, operating system functions, and so on.

Control circuitry 580 may be used to configure and operate display pixels and touch sensitive elements associated with touch-sensitive interactive skin 20. For example, control circuitry 580 may be used to illuminate or inactivate portions of interactive skin 20 to create active and inactive regions. As another example, control circuitry 580 may be used to change the operating mode of the interactive skin and/or the functional mode of interactive skin 20 based on, for example, touch-input to touch-sensitive interactive skin 20 or other user input. For example, when a user touches a virtual button on either the interactive skin 20 or on programming display 590, control circuitry 580 may take appropriate action. For example, contact between a user finger or other external object and a virtual button may direct the interactive skin 20 to take actions such as displaying information for a user. It may make a volume adjustment to media that is being played to the user. It may control media playback. It may take an action associated with a wireless communications session. Alternatively, it may take other suitable action.

One or more virtual buttons such as virtual button on the interactive skin 20 may be used to form volume adjustment switches such as sliding controls. It may form ringer s, on/off s, sleep buttons. It may also form customized buttons which may be specific to a particular program or operating system and that may change in real time during use of interactive skin 20. In another embodiment, virtual buttons may be labeled such as with particular colors, patterns, icons, text, or other information. This may assist a user in identifying the function of the button.

Touch-sensitive interactive skin 20 may have regions blocked from view using masking structures. For instance, portions of the body may block regions from view in FIG. 12A. Alternatively, a patterned opaque masking layer may be used. Regions may also be formed by inactive pixels. Control circuitry 580 may be used to configure touch-sensitive interactive skin to have regions with inactive pixels. As shown in FIG. 12A, regions may be controlled, by electrical signals applied by control circuitry to conductive traces 522.

Conductive traces 522 may be electrically coupled to control circuitry 580. Conductive traces may be control lines for display pixels in regions. Interactive skin 20 may have additional control circuitry such as control lines, drive lines, and so on along a peripheral edge of interactive skin 20. Providing interactive skin 20 with control circuitry in regions may reduce the area required for control circuitry on the peripheral edge of interactive skin 20. Providing interactive skin 20 with control circuitry in regions may also allow for multiple displays. Control circuitry may also control a plurality of interactive skins within or outside the body. They may be coupled to control circuitry 580 using a common interconnect. Connecting multiple displays to control circuitry 580 using a common interconnect may help reduce the space required for interconnects.

As shown in FIG. 12A, side surface display portions 524 may include illuminated touch-sensitive regions 526. Control circuitry 580 may be used to configure touch sensitive interactive skin 20 to illuminate pixels in illuminated touch-sensitive regions 526 and to turn off, or make inactive, remaining pixels in side display portions 524. Illuminating pixels in illuminated touch-sensitive regions 526 and making inactive other pixels in side display portions 524 may separate center surface display portion 522 from illuminated touch-sensitive regions 526.

Illuminated touch-sensitive regions 526 may be configured to remain stationary in side surface display portions 524 or may be repositioned in side surface display portions 524 during normal use of interactive skin 20 using control circuitry 580. If desired, illuminated touch sensitive regions 526 may occupy all or substantially all of side surface display portions 524. Virtual buttons 526 may be reconfigured during use of interactive skin 520. For example, interactive skin 520 may use side region 524 to display a first set of buttons when operated in one mode and may use region 524 to display a second set of buttons which may be different when operated in another mode.

A touch-sensitive region 524 may be used to form one or more selection buttons for selecting a software application to be run on interactive skin 20 using control circuitry 580. Selection buttons may include illuminated icons associate with selected software applications. The software applications may include text messaging, calendar, camera, and calculator. They may include media player, web browser, email client, cellular telephone, or other software applications. A selected software application may be activated using a touch input to a portion of illuminated touch-sensitive region 526 associated with a selected selection button. Alternatively, it may be activated by touching a region on programming display 590 of control circuitry 580 or by a manual keyboard entry mechanism. For instance, selecting a camera application button on interactive skin may cause selection buttons on illuminated touch-sensitive region 526 on interactive skin to be replaced by function buttons associated with the selected application. Alternatively, selecting a camera application button on programming display 590 of control circuitry 580 may do the same.

Illuminated touch-sensitive region 522 may display a list associated with a media player software application on interactive skin 20. In one example, illuminated touch-sensitive region 522 may display a scrollable list of song titles. Swiping edge region 524, or other region, of interactive skin in one direction may cause the illuminated touch-sensitive region 522 of interactive skin 20 to display song titles. Swiping edge region 524 or other region, of interactive skin 20 in a different direction may cause interactive skin 20 to display a different list associated with the same software application. For example, artist lists, album lists, and playlist lists. As further examples, video lists, genre lists, webcast lists, audio book lists, and so on.

More broadly speaking, the interactive skin device may be configured for accepting touch input from a user. The interactive skin device may illustratively include one or more flexible layers and may include or be mounted under a transparent display cover layer such as a layer of clear glass or plastic as previously explained. The transparent layer may be configured to hermetically seal, environmentally protect, and so on, the flexible layers lying under the transparent layer. The interactive skin may include a touch-sensitive layer that allows a user to provide touch input to the body and/or implant. Display pixels on interactive skin may be used to display visual information to the user.

The interactive skin device may be configured for detecting a condition of a body and/or at least one implant and generating an output function in response to the detected condition. The condition may be detected by a sensor. Interactive skins may be configured with display pixels used to display visual information to the user on the detected condition. Interactive skin device may be configured with a touch-sensitive layer that allows a user to provide touch input to the interactive skin device to cause the interactive skin device to check on the condition of the body and/or one or more implants or a condition of an implant or to respond to visual information provided to the user on the detected condition.

The interactive skin device may be used to support safety, communication connectivity within and without the body, and so on. The interactive skin may be used for displaying information and visual feedback to a user and for accepting input from a user.

Active portions of the interactive skin device may be used to create virtual user interface controls such as buttons. During use, the buttons or other user input interface elements may be reconfigured. For instance, the user input interface elements may be repurposed for supporting user input operations in different operating modes of the interactive skin. Virtual buttons may be provided. They may be provided additional to or in place of tactile input/output components such as physical buttons and switches.

In operation, a virtual button may be a virtual volume button. The virtual button may control audio output volume. The virtual button may be repurposed based on user input. For example, the virtual button may be repurposed to become a virtual camera shutter button for taking a picture. As another example, the virtual button may be reconfigured to serve as a controller for another device function. Images displayed on the interactive skin may indicate to a user which function is currently being performed by the virtual button. Predetermined inputs to the touch-sensitive layer such as tapping, sliding, swiping, or other motions of an external object such as a finger across the interactive skin may be used to change the operating mode of the interactive skin.

In one embodiment, interactive skin 20 may be received in a recess defined inside the body. In another embodiment the interactive skin may lie under the skin with input output functions passing through the skin of the body. In another embodiment, the interactive skin 20 may be attached to the body as previously explained. The interactive skin may be hermetically sealed by a transparent layer. The interactive skin may be configured to be environmentally friendly. The transparent layer may extend across the recess or illustratively across the entire panel. As previously explained, an opening may be provided for an audio or other output. The opening may be overlaid with output functionality friendly material. For example, for an audio output, the material may be of the kind used for outdoor speaker to keep water from ruining speakers.

The interactive skin of this disclosure may be assembled using conventional processes. For example, where interactive skin is configured using flex technology, the assembly may be in accordance with conventional flex technology processing. The interactive skin device may include an encapsulation layer including a biocompatible material. The encapsulation layer may be configured to seal the interactive skin device so as to isolate inner components of the interactive skin device from the environment of the living thing.

The interactive skin of this disclosure may be configured to be password protected so that only the user or those who have been provided the password may activate the touch feature of the interactive skin of this disclosure. In this way, the interactive skin is only touch responsive to someone who knows the password for interacting with the interactive skin. For instance, a touch may cause the interactive skin to display a keyboard for entry by a user of the password. On proper entry of the password, the interactive skin may allow further interaction by the user with the interactive skin.

Some functionality of the interactive skin of this disclosure has been previously described by illustrative examples which is not limiting. Other applications of the interactive skin of this disclosure are also covered by this disclosure. By way of further example, FIG. 13 depicts a set of functions that may be provided to the interactive skin of this disclosure. This functionality includes an audio plug receptacle 1110, a connector receptacle 2000, one or more user input components 1120, one or more output components 1160, control circuitry 1130, graphics circuitry 1170, a bus 1115, a memory 1140, a storage device 1180, communications circuitry 1150 and POM (position, orientation or movement sensor) or other sensors 1190.

Control circuitry 1130 has been previously explained and may be dedicated to an interactive skin of this disclosure or to a plurality of interactive skins of this disclosure. The control circuitry may be the control circuitry that controls a vehicle system. The control circuitry may be a control circuitry associated with a smart phone or other wireless device. The control circuitry may be a control circuitry associated with a computer device. Other control circuitry may be useable with the interactive skin of this disclosure.

Memory 1140 has been previously described and may reside in proximity or removed from the interactive skin of this disclosure. Input component and output component may provide a user with enhanced ability to interact with body and/or implant. For example, input component 1120 and output component 1160 may provide an interface for a user to interact with an application running on control circuitry.

Input component may take a variety of forms, such as a keyboard/keypad, trackpad, mouse, click wheel, button, stylus or touch screen. Input component may also include one or more devices for user authentication (e.g., smart card reader, fingerprint reader or iris scanner) as well as an audio input device (e.g., a microphone) or a video input device (e.g., a camera or a web cam) for recording video or still frames.

Output components may include any suitable display, such as a liquid crystal display (LCD) or a touch screen display, a projection device, a speaker or any other suitable system for presenting information or media to a user.

Output component 1160 may be controlled by graphics circuitry.

Graphics circuitry 1170 may include a video card, such as a video card with 2D, 3D or vector graphics capabilities. In some embodiments, output component may also include an audio component that is remotely coupled to body. For example, output component may include a headset, headphones or ear buds. These may be coupled to body with a wire or wirelessly, such as by Bluetooth headphones or a Bluetooth headset, or optically.

There may be one or more applications such as software applications stored on storage device or in memory. Control circuitry may be configured to execute instructions of the applications from memory. For example, control circuitry may be configured to execute a media player application that causes full-motion video or audio to be presented or displayed on interactive skin or an output component. Other applications may illustratively include a telephony application, a GPS navigator application, a web browser application, a calendar or organizer application. Interactive skin may also execute any suitable operating system, such as a Mac OS, Apple iOS, Linux or Windows. The system may include a set of applications stored on storage device or memory that is compatible with the particular operating system.

In some embodiments, the interactive skin of this disclosure is provided with or coupled to communications circuitry to connect to one or more communications networks. Communications circuitry 1150 may be any suitable communications circuitry operative to connect to a communications network and to transmit communications (e.g., voice or data) from interactive skin or implant coupled to interactive skin to other devices within the communications network. Communications circuitry may be operative to interface with the communications network. The communications circuitry may do so using any suitable communications protocol such as, Wi-Fi (such as., an 802.11 protocol), Bluetooth, high frequency systems (such as, 900 MHz, 2.4 GHz and 5.6 GHz communication systems), infrared, GSM, GSM plus EDGE, CDMA, quad band and other cellular protocols, VOIP or any other suitable protocol.

Communications circuitry may be operative to create a communications network using any suitable communications protocol. Communications circuitry may create a short-range communications network to connect to other devices using a short-range communications protocol. For instance, communications circuitry may be operative to create a local communications network using the Bluetooth protocol to couple to a Bluetooth headset or other Bluetooth device. Communications circuitry may include a wired or wireless network interface card (NIC) configured to connect to the Internet or any other public or private network. For instance, interactive skin may be configured to connect to the Internet via a wireless network. The network may be packet radio network, an RF network, a cellular network or any other suitable type of network. Communication circuitry may initiate and conduct communications with other communications devices or media devices within a communications network.

The interactive skin of this disclosure may be provided with or coupled to other components suitable for performing a communications operation. For instance, the interactive skin may include or have associated with it a power supply. The power supply may be a battery, a lithium battery, a solar battery, and so on. The power supply may be provided by other sources, such as supplied by a computing device, such as a smartphone, associated with the interactive skin.

As other examples, the interactive skin may include or have associated with it an antenna, ports or interfaces for coupling to a host device, a secondary input mechanism such as an ON/OFF switch or any other suitable component.

The interactive skin of this disclosure may be provided with or coupled to POM or other sensors. These sensors may be used to determine the approximate geographical or physical location of interactive skin. This may allow the location of an interactive skin or its associated implant or other implants in communication therewith to be derived from any suitable trilateration or triangulation technique. In this illustrative example, POM sensors may include an RF triangulation detector or sensor or any other location circuitry configured to determine the location of interactive skin and/or its associated implants.

POM sensors 1190 provided with or coupled to interactive skin may also include one or more sensors or circuitry for detecting the position orientation or movement of interactive skin or an implant or implants associated with interactive skin. Such sensors and circuitry may illustratively include single-axis or multi-axis accelerometers, angular rate or inertial sensors (such as, optical gyroscopes, vibrating gyroscopes, gas rate gyroscopes or ring gyroscopes), magnetometers (such as, scalar or vector magnetometers), ambient light sensors, proximity sensors, motion sensor (such as, a passive infrared (PIR) sensor, active ultrasonic sensor or active microwave sensor) and linear velocity sensors. For instance, control circuitry may be configured to read data from one or more of POM sensors in order to determine the location orientation or velocity of an interactive skin or implant or implants associated therewith. One or more of POM sensors may be positioned above, below or on either side of the display presented by the interactive skin of this disclosure. The sensor may also be positioned near an output component such as a speaker.

Other sensors may also be provided such as explained below.

Control circuit 1130 may be powered by a power source. The power source may be a battery, such as a lithium battery, a solar panel, etc. In an embodiment wherein the control circuity is provided by a computing device such as a smart phone, mobile computing or other computing device, the power source of the device may power the control circuitry. The interactive skin of this disclosure may be provided with its own dedicated power source sized to meet the power requirements demanded by the functionality provided by the interactive skin. The battery may be included within an encapsulation layer including a biocompatible material. The encapsulation layer may be configured to seal the interactive skin device so as to isolate inner components of the interactive skin device from the environment of the living thing.

Software may be used to manage power consumption by the interactive skin. For example, power to the interactive skin may be throttled based on power source requirements. For instance, when available power falls below predetermined levels, power to the interactive skin may be turned entirely off or functionality provided by the interactive skin may be throttled back.

The interactive skin may be provided with varying combinations of the foregoing electronic components. For example, an interactive skin may be provided with a GPS sensor and a controller and communication circuitry to allow the whereabouts of the interactive skin or implant associated therewith to be tracked. This may allow people to be tracked and found such as if medical conditions warrant. As another example, an interactive display may include an audio jack. Any combination of components to configure the interactive skin with the desired smarts may be used to achieve the desired functionality.

Additionally, the body may include other electronic functionality, such as a loudspeaker 1194 or microphone 1192 to enable a user to interact with the interactive skin in this way.

As another example, interactive skin may be configured with a temperature sensor configured to generate a change in state upon detection of a predetermined temperature. For example, if the temperature rises above a predetermined temperature, the interactive skin may generate an alert, thereby indicating to the user that there is an over-heating condition in the body. The change in temperature may be used for other medical purposes such as tracking ovulation.

The condition detected by the sensor used in connection with the interactive skin of this disclosure may be selected from the group consisting of at least temperature, pressure, current, voltage, incorrect electrical connection, etc. The response of the interactive skin to a condition detected by the sensor may be selected from the group consisting of audible alert, visual alert, or combination thereof. Responsive to a detected condition, the interactive skin of this disclosure may provide an audible alert or present a display indicating the detected condition.

The interactive skin may be configured to be touch-sensitive as previously described to allow user to interact with the interactive skin. For instance, on touch the interactive skin may provide the current condition of the body and/or implant with which the interactive skin is associated, such as current temperature reading by sensor. Further user interaction may cause the interactive display to display historical information on the body and/or implant or provide other information. The user may interact with the interactive display in accordance with the teachings of this disclosure to learn more about the condition of the body and/or implant with which the interactive skin is associated or to instruct the interactive skin to take some action such as change mode operation, change configuration, reset configurations, Responsive to the detected condition, the interactive skin may communicate the condition to an electronic component and thereby provides a notification service. In one example, the interactive skin may communicate the condition to a smart phone. The interactive skin may communicate information about the detected condition such as the existence of the condition, severity of condition, time remaining before failure, remedial steps that may be taken, and so on.

As explained in this disclosure, an implantable medical device for use with this disclosure is an implantable medical device that once implanted may generate a signal indicative of a physical parameter of a body. Through wire, wireless, or optical connection of the interactive skin device 20 to the implantable medical device, the interactive skin device 20 of this disclosure may monitor the signals generated by the implantable medical device that are indicative of a physical parameter of a body. An implantable medical device that satisfies this disclosure may be used with this disclosure.

As another example, reference is made to FIG. 14 showing ECG electrode placement in a 12-lead electrocardiogram in an implanted configuration according to this disclosure.

In the embodiment of FIG. 15 of this disclosure, the implantable medical device are electrodes configured to generate signals for an electrocardiogram.

The term ECG or EKG usually refers to a 12-lead electrocardiogram, a well-known standard for measuring the heart's electrical pattern. A 12-lead ECG is a professional version that is administered in a clinic or hospital setting. Twelve leads (using 10 electrodes) are placed on a person's limbs and across the torso. They measure the heart's electrical activity in several directions and planes and are highly sensitive. They can detect abnormal electrical patterns and find areas where heart muscle is dying, as in the case of inadequate blood supply or heart attack.

Conventional electrocardiographs use a machine to perform electrocardiography once the patient is hooked up with the leads at the medical facility. The machine produces the electrocardiogram from the signals generated by the leads.

More recent advancements in electrocardiography include work in diminishing the size of the unit to make it more portable and therefore more accessible to larger groups of patients. To achieve this, these smaller devices rely on fewer electrodes, like only two electrodes which together deliver "lead I" of the standard ECG.

Companies are devising wearables to monitor heart conditions. One company, Apple, has devised an application that effectively performs as a single-lead ECG. Other companies are working in this area.

In a 12-lead electrocardiogram, leads are broken down into three types: limb; augmented limb; and precordial or chest. The 12-lead ECG has a total of three limb leads and three augmented limb leads arranged like spokes of a wheel in the coronal plane(vertical), and six precordial leads or chest leads that lie on the perpendicular transverse plane (horizontal).

Figure 14A:
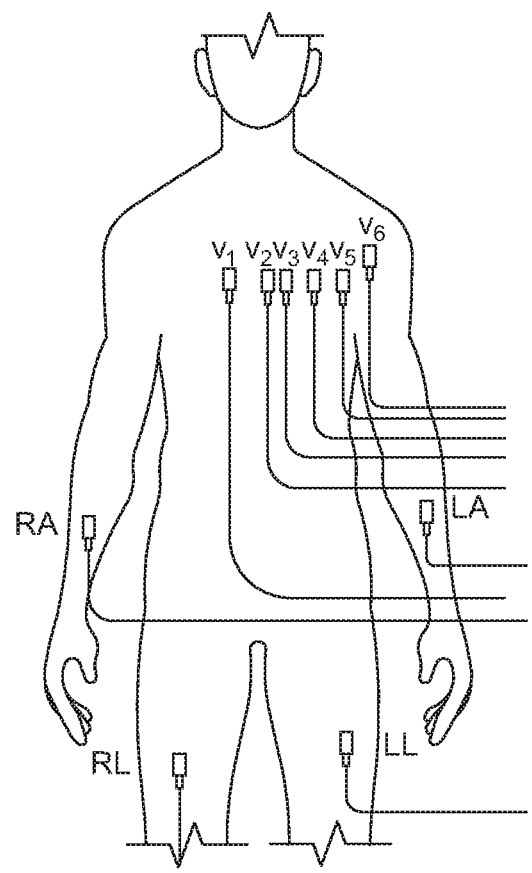
FIGS. 14A, 14B (collectively, FIG. 14) depict an illustrative embodiment of the present disclosure.
Figure 14B:
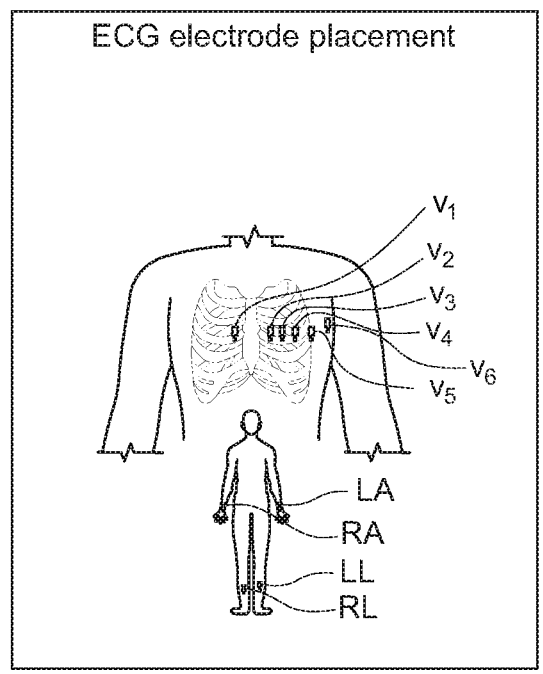

The 10 electrodes in a 12-lead ECG are listed below. The placement of the 10 wired electrodes on the body are depicted in FIG. 14A. According to this disclosure, electrodes may be configured as implantable medical devices according to this disclosure. FIG. 14B shows the location on the body where the wireless electrodes may be implantedly placed according to this disclosure. The following table explains each electrode and placement.

| Electrode name | Electrode placement |
|---|---|
| RA | On the right arm, avoiding thick muscle. |
| LA | In the same location where RA was placed, but on the left arm. |
| RL | On the right leg, lower end of inner aspect of calf muscle. (Avoid bony prominences) |
| LL | In the same location where RL was placed, but on the left leg. |
| $V_1$ | In the fourth intercostal space (between ribs 4 and 5) just to the right of the sternum (breastbone). |
| $V_2$ | In the fourth intercostal space (between ribs 4 and 5) just to the left of the sternum. |
| $V_3$ | Between leads $V_2$ and $V_4$. |
| $V_4$ | In the fifth intercostal space (between ribs 5 and 6) in the mid-clavicular line. |
| $V_5$ | Horizontally even with $V_4$, in the left anterior axillary line. |
| $V_6$ | Horizontally even with $V_4$ and $V_5$ in the mid-axillary line . . . |

FIG. 15 depicts an electrocardiographic data monitoring system of this disclosure wherein one or more or all of the electrodes are implanted. FIG. 15A depicts implantable medical devices configured as electrodes that are implanted and interconnected through implanted hardwiring in electrocardiographic data monitoring system 601. FIG. 15B depicts implantable medical devices configured as electrodes that are implanted and interconnected wirelessly or through a wireless and implanted wired combination in electrocardiographic data monitoring system 602.

In either example, the electrocardiographic data monitoring system 601, 602 may include one or more ECG acquisition devices implanted into a human. These ECG acquisition devices are depicted as one or more of electrodes RA, LA, RL, LL, V1, V2, V3, V4, V5, and V6.

A processor may be configured to receive data from the at least one implanted ECG acquisition device, wherein the processor is configured to process the one or more ECG acquisition device data and to generate an output based on the processed data.

In one aspect, the processor may be a processor implanted into the body. For example, the processor may be incorporated into an implanted circuit, like on implanted electronic device 610 in FIG. 15A and implanted circuits 632, 634, 635, 636, 637 in FIG. 15B, wherein the processor is denoted by the letter "P".

As one example, the implanted circuit device 610 in FIG. 15A may be configured to receive data from the at least one implanted ECG acquisition device, wherein the processor is configured to process the one or more ECG acquisition device data and to generate an output based on the processed data. In one example, the output based on the processed data may be transmitted via implanted hardwire 650 to an interactive skin device 20 for use in accordance with the teachings of an interactive skin device of this disclosure.

Alternatively, the implanted circuit device 610 may be configured with a port on the end of member 611 (or elsewhere on the implanted circuit device 610) like manner as port 320 of the interactive skin device of this disclosure and located in or proximate to the epidermis, for example. With such a port, the output from the implanted circuit device 610 based on the processed data may be transmitted via external hardwire 642 to an interactive skin device 20 for use in accordance with the teachings of an interactive skin device of this disclosure. In this case, connector 641 may plug into the port on the implanted circuit device and connector 643 into port 320 (FIG. 11B) of the interactive skin device. Alternatively, connector 661 may plug into the port on the implanted circuit device and connector 663 into a port of a computing device, like a smart phone 620.

As another example, a processor on one or more of the implanted circuits 632, 634, 635, 637, 637 in FIG. 15B may be configured to receive data from the at least one implanted ECG acquisition device, wherein the processor is configured to process the one or more ECG acquisition device data and to generate an output based on the processed data. In one example, the output based on the processed data may be transmitted wirelessly 32 to an interactive skin device 20 for use in accordance with the teachings of an interactive skin device of this disclosure. Alternatively, the output based on the processed data may be transmitted wirelessly 32' to an external computer, like a smart phone 622

In a different aspect, the processor configured to receive data from the at least one implanted ECG acquisition device, wherein the processor is configured to process the one or more ECG acquisition device data and to generate an output based on the processed data may be the processor incorporated into an interactive skin device 20 or an external computing device, like a smart phone 620. In one aspect, the processors previously described as being implanted in the body may be configured as signal processors configured to process and communicate the signals generated by the one or more ECG acquisition devices implanted into a human to the interactive skin device or the external computing device, like a smart phone.

In the processors previously disclosed, each processor may be associated with a memory. In FIG. 15B, the memory is designated with the letter "M" and it is similarly designated in FIG. 15A in the embodiment wherein implanted circuit device 610 may be used with a processor.

Wireless communication circuits in FIG. 15B are depicted with the letters "TX" and "RX", short for transmitters and receivers. If electronic device is configured with a communication circuit, the communication circuit may be wireless communication circuits or hardwire circuits. Communication circuit is depicted in FIG. 15A with the letter "C"

As seen in FIG. 15, ten implanted electrodes that may form a 12-lead electrocardiogram. The one or more ECG acquisition devices may include ten implanted electrodes. As explained, these may be electrodes for RA, LA, RL, LL, V1, V2, V3, V4, V5, and V6. These electrode may be in electrical communication with at least one processor and memory, as explained. See, for instance processors "P" and the processors in the interactive skin and external computing device like smart phone in FIG. 15. These electrodes may also be in electrical communication with a communication circuit. A first of the ten implanted electrodes may be implantably positioned on a right arm below an outside surface of epidermis of the human. A second of the ten implanted electrodes may be implantably positioned on a left arm below an outside surface of epidermis of the human. A third of the ten implanted electrodes may be implantably positioned on a left leg below an outside surface of epidermis of the human. A fourth of the ten implanted electrodes may be implantably positioned on a right leg below an outside surface of epidermis of the human. A fifth of the ten implanted electrodes may be implantably positioned as a precordial lead V1 at the 4th intercostal space on the right side of the sternum below an outside surface of epidermis of the human. A sixth of the ten implanted electrodes may be implantably positioned as a precordial lead V2 at the 4th intercostal space on the left side of the sternum below an outside surface of epidermis of the human. A seventh of the ten implanted electrodes may be implantably positioned as a precordial lead V3 at the 5th intercostal space midway between V4 and V2 below an outside surface of epidermis of the human. An eighth of the ten implanted electrodes may be implantably positioned as a precordial lead V4 at the 5th intercostal space midclavicular below an outside surface of epidermis of the human. A ninth of the ten implanted electrodes may be implantably positioned as a precordial lead V5 at the 5th intercostal space midway between V4 and V6 below an outside surface of epidermis of the human. A tenth of the ten implanted electrodes may be implantably positioned as a precordial lead V6 at the 5th intercostal space midaxillary below an outside surface of epidermis of the human.

From the foregoing disclosure, it is seen that an implanted processor may be configured to process the one or more ECG acquisition device data and to generate an output based on the processed data. The output may be communicated to an interactive skin device or an external computer like a smart phone. It is also seen that an external processor, such as in an interactive skin device or an external computer like a smart phone, may be configured to process the one or more ECG acquisition device data and to generate an output based on the processed data.

Figure 16:
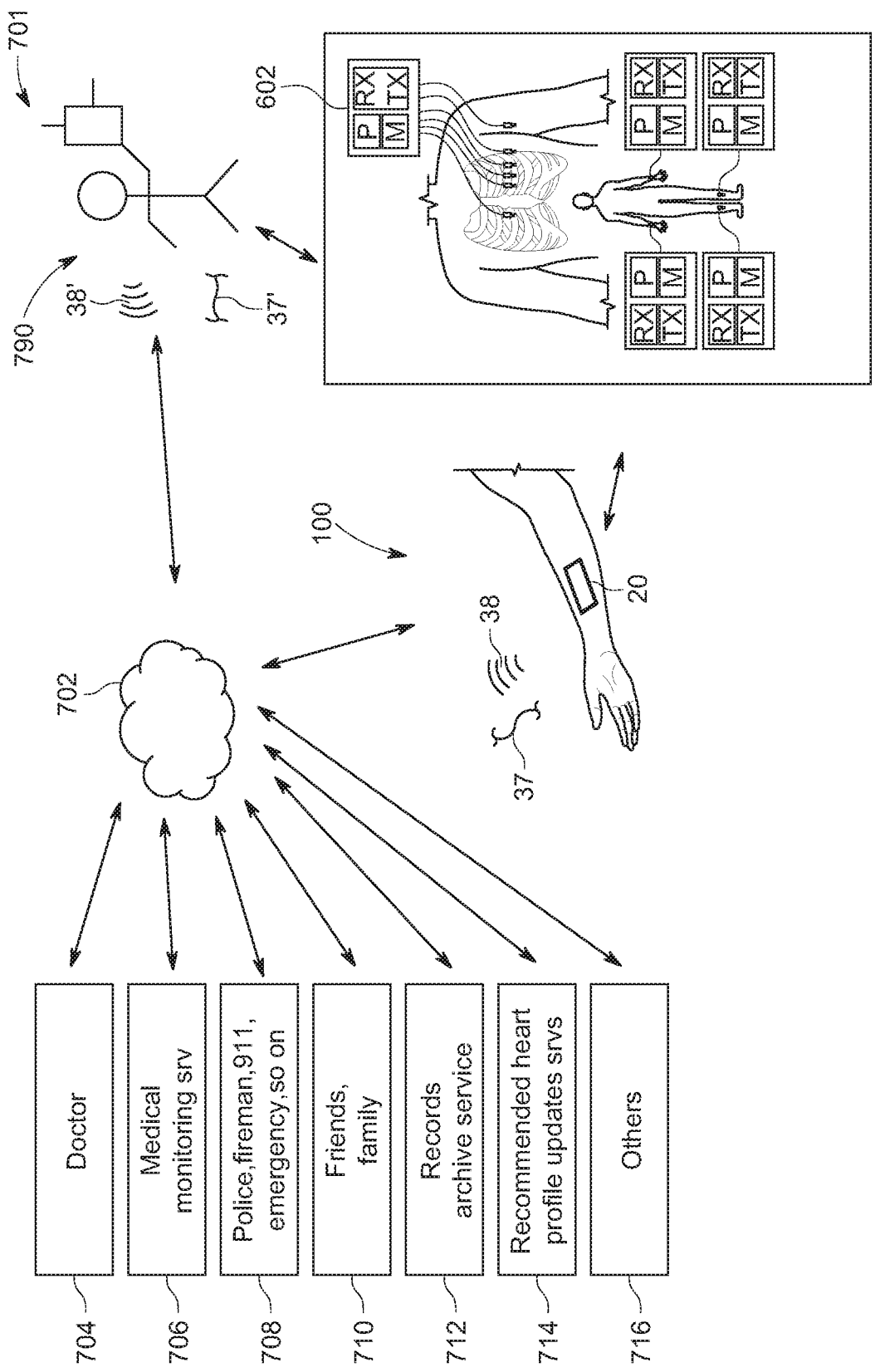
FIG. 16 depicts an illustrative embodiment of the present disclosure.

Which implanted electrode used in the electrocardiogram system to process the implanted electrode data and to generate an output based on the processed data is a matter of design choice guided by the teachings of this disclosure In either case, the processed data may be communicated throughout a network in a system 701 as depicted in FIG. 16. The network may be a public or a private network. The interactive device may trigger an alert when the at least one monitored physical parameter deviates from a predetermined threshold.

More specifically, in one aspect, implanted processor in electrocardiographic data monitoring system 602 may be configured to process the one or more ECG acquisition device data and to generate an output based on the processed data. The output may be communicated to an interactive skin device 20 or an external computing device, in one example a smart phone 790; all as previously explained. The interactive skin device 20 or external computing device, like a smart phone, may transmit the output based on the processed data or may manipulate that output based on the processed data to generate other output data based on the output based on the processed data. The transmission may be by wire 37, 37' or wirelessly 38, 38'.

In FIG. 16, the transmitted data is depicted to be transmitted through a network such as through a cloud 702 to one or more computing devices in the cloud 702 that may be in communication with the interactive skin device 20 or an external computing device, like the smart phone 790. Illustratively the computing device receiving the transmission may include a doctor 704; a medical monitoring service 706; a police, fireman, 711, so service; friends, family 710; records, archive services 712; recommended heart profile updates 714; others 716.

The transmission provides ECG data to any of these or other recipients in the system 701 which enables the recipient to act on the ECG data as needed. For instance, the transmission may be an alert that may be triggered when at least one monitored ECG physical parameter deviates from a predetermined threshold. The recipients may proceed accordingly. For example, if the deviation from the predetermined threshold is critical, 911 may immediately dispatch an ambulance, the doctor may immediately schedule to be at the hospital, family and friends may immediately go to the location of the person transmitting the alert or to the hospital, and so on. System 701 may be configured for bidirectional communication between the person originating the ECG data and the receiving computing device within the system. Thus, a doctor may communicate to the person through the interactive skin device or computing device, like the smart phone. As another example, recommended heart profile updates service may download to the interactive skin device or computing device like a smart phone of the person updated heart profile information for use in setting alerts.

Figure 17:
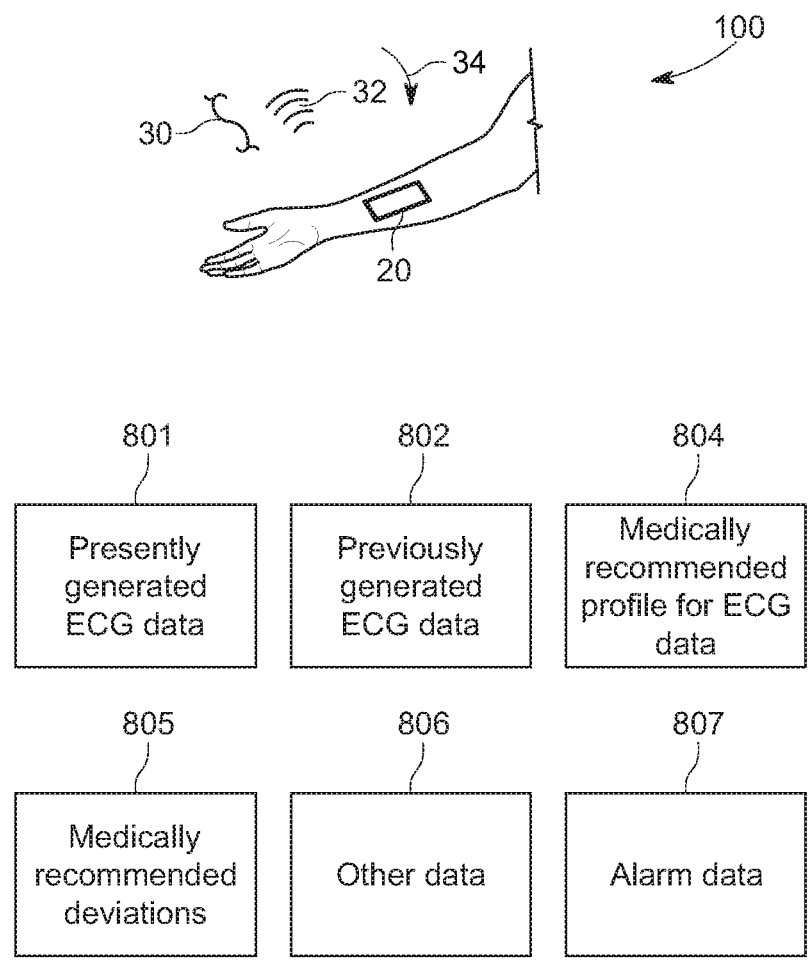
FIG. 17 depicts an illustrative embodiment of the present disclosure.

FIG. 17 depicts an illustrative aspect for setting alerts applicable to any of the embodiments of this disclosure. The ECG data from the system of this disclosure may be generated continually, periodically, or on-demand. In addition, the generated ECG data may be displayed continually or periodically or on demand. For instance, the system may continually generate ECG data on the heart. Alternatively, the system may generate ECG data at predetermined periods of time such as every 5 minutes. In an alternative embodiment, the ECG data may be generated on command by the user.

In one embodiment, any one or more processor as previously disclosed that may be configured to receive data from the at least one implanted ECG acquisition device, wherein the processor is configured to process the one or more ECG acquisition device data and to generate an output based on the processed data may be provided with instructions stored in a memory. The instructions may cause the processor to store presently generated ECG data 801 in one memory location; store previously generated ECG data 802 in a memory location; store a medically recommended profile 804 pertinent to the ECG physical parameter in another memory location; medically recommended deviations 805 pertinent to the ECG physical parameter (for example, thresholds outside of which the deviation of the ECG physical parameter may be an alarming condition) in another location; store other data 806 like body vital data like temperature, heart rate, and so on data made possible by implanted medical devices according to this disclosure in another memory location; alarm data 807 in another location.

In one aspect, the instructions may cause the processor to continually or periodically or on demand compare the presently generated ECG data 801 to the profile pertinent to the ECG physical parameter the processor is processing 804 to determine any deviation. The instructions may cause the processor to compare the determined deviation to medically recommended deviations 805. The instructions may cause the processor to trigger an alarm if the comparison shows a deviation outside of the threshold for an alarming condition.

In another aspect, the instructions may instruct the processor to check other information 806 like the vitals of the person and then pull a medically recommended profile 804 based upon such information to do a comparison, such as of the kind previously explained, in this case determining a deviation with respect to a profile based on the other information 806 like the vitals of the person.

The ECG generated at any moment may be time-stamped and stored in location 802 for use in monitoring the heart going forward. The time-stamped ECG generated data may be stored in the memory of any computing device in communication with the processor.

The algorithm employed may make a comparison of any frame of ECG generated data. For instance, the algorithm may compare a current frame of ECG generated data to one or more frames of ECG generated data over different time periods. Variations between any two or more frames of ECG generated data may be determined and any variation that may indicate the presence of a condition on the heart that may be harmful or cause for concern or medical intervention may trigger an alarm.

In addition, the ECG data generated at any moment may be compared to one or more profiles for ECG data recommended by medical or other professionals 804. The one or more profiles for ECG data recommended by medical or other professionals. May be stored in the memory of any computing device as explained herein. The algorithm may make the comparison using the instant frame or any previous frame of ECG generated data or both. For instance, the algorithm may compare a current frame of ECG generated data against one or more profiles for ECG data recommended by medical or other professionals. Alternatively, the algorithm may compare a previous frame or a plurality of frames against one or more profiles for ECG data recommended by medical or other professionals. Variations between any two or more frames of ECG generated data may be determined and any variation that may indicate the presence of a condition on the heart that may be harmful or cause for concern or medical intervention may trigger an alarm 450

In accordance with this disclosure, the wired and/or wireless electrodes may be in electrical communication with any computing device. The computing device may be the interactive skin 20. Alternatively, the computing device may be a computing device like a smart phone, a smart watch, a mobile computing device, a personal computing device, or other computing device.

As explained, FIG. 17 depicts an illustrative aspect for setting alerts applicable to any of the embodiments of this disclosure. While the specific example illustrated application of alerts for electrodes of an electrocardiogram, they are applicable to all of the teachings of this disclosure. For example, the physical parameters monitored by the interactive skin of this disclosure from implants depicted in FIG. 1 may be determined and stored as in 801, stored historically as in 802, be compared to medically recommended parameter data or profiles 804, generate and store alarms 807 and so on, all as taught in this disclosure.

FIG. 15B teaches an illustrative disclosure wherein ten electrodes may form a 12-lead electrocardiogram In another aspect, the one or more ECG acquisition devices may include a first ECG acquisition device, a second ECG acquisition device, a third ECG acquisition device, a fourth ECG acquisition device, and a fifth ECG acquisition device. The first ECG acquisition device may include a first implanted electrode being implantably positioned on a right arm below an outside surface of epidermis of the skin of a human and in electrical communication with a first processor, memory, and a communication circuit. The second ECG acquisition device may include a second implanted electrode being implantably positioned on a left arm below an outside surface of epidermis of the skin of a human and in electrical communication with a second processor, memory, and a communication circuit. The third ECG acquisition device may include a third implanted electrode being implantably positioned on a left leg below an outside surface of epidermis of the skin of a human and in electrical communication with a third processor, memory, and a communication circuit. The fourth ECG acquisition device may include a fourth implanted electrode being implantably positioned on a right leg below an outside surface of epidermis of the skin of a human and in electrical communication with a fourth processor, memory, and a communication circuit. The fifth ECG acquisition device may include a fifth implanted electrode being implantably positioned as a precordial lead V1 at the 4th intercostal space on the right side of the sternum, a sixth implanted electrode being implantably positioned as a precordial lead V2 at the 4th intercostal space on the left side of the sternum a seventh implanted electrode being implantably positioned as a precordial lead V3 at the 5th intercostal space midway between V4 and V2, an eighth implanted electrode being implantably positioned as a precordial lead V4 at the 5th intercostal space midclavicular, a ninth implanted electrode being implantably positioned as a precordial lead V5 at the 5th intercostal space midway between V4 and V6, a tenth implanted electrode being implantably positioned as a precordial lead V6 at the 5th intercostal space midaxillary. The fourth, fifth, sixth, seventh, eighth, ninth, and tenth implanted electrodes device may be in electrical communication with a fifth processor, memory, and a communication circuit of the fourth fifth ECG acquisition device. The first ECG acquisition device, the second ECG acquisition device, the third ECG acquisition device, the fourth ECG acquisition device, and the fifth ECG acquisition device may be in electrical communication with the processor configured to process the ECG acquisition device data and to generate an output based on the processed data. The ten electrodes may form a 12-lead electrocardiogram. The processor configured to process the one or more ECG acquisition device data and to generate an output based on the processed data may trigger an alert when a physical parameter from at least one of the 12-leads deviates from a predetermined threshold.

In another aspect, the one or more ECG acquisition devices may include three implanted electrodes in electrical communication with the processor configured to process the ECG acquisition device data and to generate an output based on the processed data. A first of the three implanted electrodes device may be implantably positioned on a right arm below an outside surface of epidermis of the skin of a human. A second of the three implanted electrodes may be implantably positioned on a left arm below an outside surface of epidermis of the skin of a human. A third of the three implanted electrodes may be implantably positioned on a left leg below an outside surface of epidermis of the skin of a human. The three electrodes may form a 3-lead electrocardiogram. The processor configured to process the one or more ECG acquisition device data and to generate an output based on the processed data may trigger an alert when a physical parameter from at least one of the 3-leads deviates from a predetermined threshold.

In another aspect, the electrocardiographic data monitoring system of the previous example may further include a fourth electrode implantably positioned on a right leg below an outside surface of epidermis of the skin of a human and in electrical communication with the processor configured to process the ECG acquisition device data and to generate an output based on the processed data. The four electrodes may form a 4-lead electrocardiogram. The processor configured to process the one or more ECG acquisition device data and to generate an output based on the processed data may trigger an alert when a physical parameter from at least one of the 4-leads deviates from a predetermined threshold.

In another aspect, an electrocardiographic data monitoring system may include one implanted electrode in electrical communication with the processor configured to process the ECG acquisition device data and to generate an output based on the processed data. The implanted electrode may be positioned on an arm below an outside surface of epidermis of the skin of a human. The one electrode may form a 1-lead electrocardiogram. The processor configured to process the one or more ECG acquisition device data and to generate an output based on the processed data may trigger an alert when a physical parameter from at least one of the 1-lead deviates from a predetermined threshold. The arm may be a left arm.

Figure 18A:
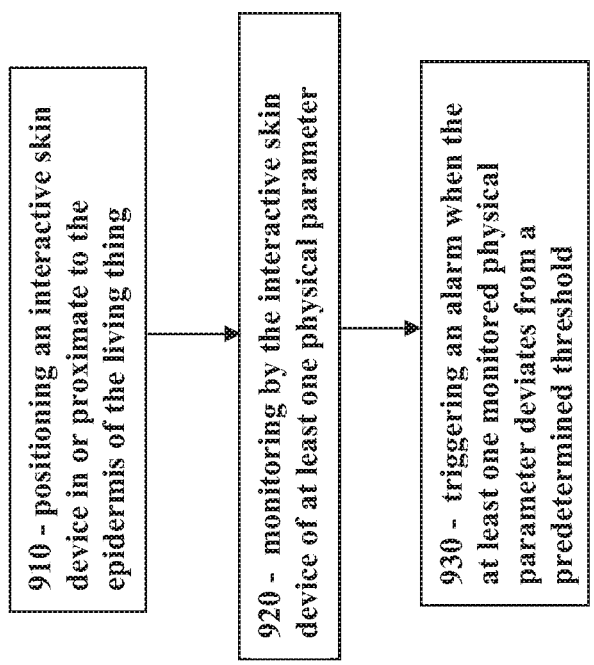
FIGS. 18A, 18B, 18C (collectively, FIG. 18) depict illustrative methods of the present disclosure
Figure 18B:
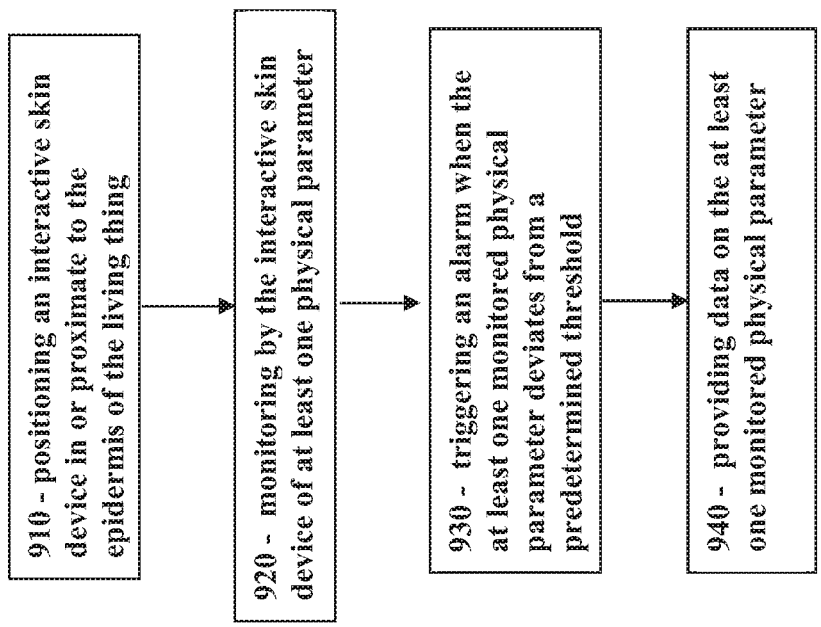
Figure 18C:
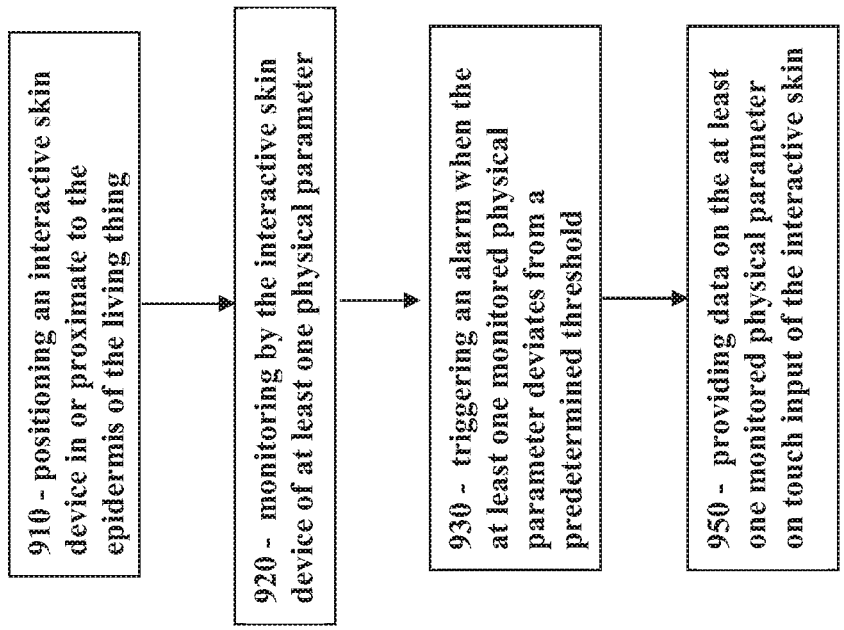

In another aspect is a method for monitoring physical parameters of a living thing. As depicted in FIG. 18, the method may include positioning an interactive skin device in or proximate to the epidermis of the living thing 910; monitoring by the interactive skin device of at least one physical parameter generated by an implanted medical device 920; and triggering an alarm when the at least one monitored physical parameter deviates from a predetermined threshold 930.

The method may further include providing data on the at least one monitored physical parameter 940.

The method may include providing data on the at least one monitored physical parameter on touch input of the interactive skin device 950.

The method may include communicating data on the at least one monitored physical parameter to an external device.

The method may include proximally positioning the interactive skin device below the epidermis of the living thing.

The method may include proximally positioning the interactive skin device outside the epidermis of the living thing.

The method may include sealing the interactive skin device inside the epidermis of the living thing with a biocompatible material.

The method may include comprising projecting a visual display from the interactive skin device through the epidermis.

The method may further include rendering a visual display projected from the interactive skin on the epidermis.

There is thus disclosed an interactive skin device for monitoring physical parameters of a body of a living thing.

The interactive skin device may be positioned in or proximate to the skin of the living thing. The interactive skin device may monitor at least one physical parameter generated by an implanted medical device. The interactive device may include a flexible display layer 22, a cover layer 26, and a control circuit. The control circuit may be configured to control operation of the flexible display layer. The interactive skin device may trigger an alert when the at least one monitored physical parameter deviates from a predetermined threshold.

The interactive skin device may include a touch sensitive layer 24 and the control circuit may be configured to control operation of touch sensitive elements. The cover layer may include a transparent display cover layer 26.

The living thing may be a human. In another embodiment, the living thing may be an animal.

The interactive skin may provide data on the at least one monitored physical parameter.

The interactive skin may provide data on the at least one monitored physical parameter on touch input of the interactive skin device.

The interactive skin device may include a communication circuit. The communication circuit may be configured to communicate with an external computing device.

The interactive skin device may include a communication circuit. The communication circuit may be configured to communicate with the implanted medical device.

The external computing device may be selected from the group consisting of a smart phone, portable computer, personal computer, and server computer.

The proximate positioning of the interactive device may be below the epidermis of the living thing.

The implanted interactive skin device may include an encapsulation layer including a biocompatible material. The encapsulation layer may be configured to seal the interactive skin device so as to isolate inner components of the interactive skin device from the environment of the living thing.

The alert may be selected from the group consisting of a transdermal visual display and an auditory display.

The visual display rendered on the flexible display layer may be projected through the epidermis.

The cover layer may include at least one raised pattern that may be recognized through the epidermis on touch. The at least one raised pattern may be associated with at least one function of the interactive skin device. Touch of the at least one raised pattern may activate the at least one function.

The proximate positioning of the interactive device may be outside the epidermis of the human.

The interactive skin device may include an interactive skin device supporting layer disposed between the interactive skin device and the epidermis.

The interactive skin device supporting layer may be an adhesive. The adhesive may be adapted to a portion of the epidermis. The interactive skin device may be adapted to a portion of the adhesive.

The adhesive may be an epidermal adhesive.

The interactive skin device may include an interactive skin device supporting member configured to hold the interactive skin device in a spatial relationship with respect to the epidermis.

The interactive skin device supporting member may include one or more connectors configured for attaching the interactive skin device to the human.

The one or more connectors may include one or more adhesive spots disposed on the epidermis configured for attaching the interactive skin device to the human when the interactive skin device is placed against the one or more adhesive spots.

The one or more connectors may be surgical stitches.

The one or more connectors may be surgically attached to the body.

The one or more connectors may be one of a pair of a Velcro hook and loop fastener surgically attached to the human, an other of the pair of a Velcro hook and loop fastener being attached to the interactive skin device, and the engagement of the one and the other of the pair of a Velcro hook and loop fastener being the attachment of the interactive skin device to the human.

The interactive skin device supporting layer disposed between the interactive skin device and the epidermis may be a sleeve configured to be worn about a portion of the body of the human. The interactive skin device being adapted to a portion of the sleeve.

The sleeve may include a biocompatible material.

The interactive skin device may be adapted to a ventral portion of the sleeve and the sleeve may be disposed about a forearm of the human.

The interactive skin device may include a supporting member configured to hold the interactive skin device in a spatial relationship to the sleeve.

The interactive skin device to sleeve supporting member may include one or more connectors configured for attaching the interactive skin device to the sleeve.

The one or more connectors may be one of a pair of a Velcro hook and loop fastener surgically attached to the sleeve, an other of the pair of a Velcro hook and loop fastener may be attached to the interactive skin device, and the engagement of the one and the other of the pair of a Velcro hook and loop fastener may be the attachment of the interactive skin device to the sleeve.

The one or more connectors may be stitches.

The interactive skin device may be adapted to a ventral portion of the sleeve and the sleeve may be disposed about at least a portion of a forearm and upper arm of the human.

The interactive skin device may be adapted to a ventral portion of the sleeve and the sleeve is disposed about a thigh of the human.

The implanted interactive skin device may include a port selected from the group consisting of an input port and an output port. The epidermis of the human may be provided with an opening configured for enabling an electrical connection between an external wire connector and the port.

The interactive skin device may include a sealant layer. The sealant layer may be disposed across the port when the port is not being used. The sealant layer may be configured to seal the implanted interactive skin device so as to protect the human from infection from the opening in the epidermis.

The implanted interactive skin device may include a member that extends into the epidermis. The port defined in the implanted interactive skin device may open into the epidermis of the human.

The implanted interactive skin device may include a sealant plug. The sealant plug may be configured to being disposed in the port defined in the implanted interactive skin device when the port is not being used. The sealant plug may protect the human from infection from the opening in the epidermis.

The external wire connector may be configured to connect the implanted interactive skin device to an external computing device.

The external computing device may include a smart phone, portable computer, personal computer, server computer, or other computing device.

The implanted medical device may include a deep brain neurostimulator, a gastric stimulator, a foot drop implant, a cochlear implant, a cardiac defibrillator, a pacemaker, and an insulin pump.

The implanted medical device may include an orthopedic implants, cardiovascular implants, spinal implants, neurostimulators, ophthalmic implants dental implants, breast implants, facial implants, drug-eluting medical implants, The implanted medical device may be a drug-eluting medical implant, the drug-eluting medical implant selected from the group consisting of drug-eluting vascular stents, drug-eluting wound dressings and protein-eluting scaffolds for tissue regeneration.

The implanted medical device may be wired, optical or wireless.

The one or more biocompatible materials may include metallic biomaterials, ceramic biomaterials, polymers biomaterials, natural biomaterials, and glass.

The communication circuitry may be wireless communication circuitry, wired communication circuitry, optical communication circuitry.

The communication between the communication circuit and the external computing device may be over a network.

In another aspect, an electrocardiographic data monitoring system is disclosed. The electrocardiographic data monitoring system may include one or more ECG acquisition devices implanted into a human. A processor may be configured to receive data from the at least one implanted ECG acquisition device. The processor may be configured to process the one or more ECG acquisition device data and to generate an output based on the processed data.

The one or more ECG acquisition devices may include ten implanted electrodes in electrical communication with at least one processor, memory, and a communication circuit. A first of the ten implanted electrodes may be implantably positioned on a right arm below an outside surface of epidermis of the human. A second of the ten implanted electrodes may be implantably positioned on a left arm below an outside surface of epidermis of the human. A third of the ten implanted electrodes may be implantably positioned on a left leg below an outside surface of epidermis of the human. A fourth of the ten implanted electrodes may be implantably positioned on a right leg below an outside surface of epidermis of the human. A fifth of the ten implanted electrodes may be implantably positioned as a precordial lead V1 at the 4th intercostal space on the right side of the sternum below an outside surface of epidermis of the human. A sixth of the ten implanted electrodes may be implantably positioned as a precordial lead V2 at the 4th intercostal space on the left side of the sternum below an outside surface of epidermis of the human. A seventh of the ten implanted electrodes may be implantably positioned as a precordial lead V3 at the 5th intercostal space midway between V4 and V2 below an outside surface of epidermis of the human. An eighth of the ten implanted electrodes may be implantably positioned as a precordial lead V4 at the 5th intercostal space midclavicular below an outside surface of epidermis of the human. A ninth of the ten implanted electrodes may be implantably positioned as a precordial lead V5 at the 5th intercostal space midway between V4 and V6 below an outside surface of epidermis of the human. A tenth of the ten implanted electrodes may be implantably positioned as a precordial lead V6 at the 5th intercostal space midaxillary below an outside surface of epidermis of the human. The at least one processor of the one or more ECG acquisition devices may be in electrical communication with the processor configured to process the one or more ECG acquisition device data and to generate an output based on the processed data. The ten implanted electrodes may be form a 12-lead electrocardiogram. The processor configured to process the one or more ECG acquisition device data and to generate an output based on the processed data may trigger an alert when a physical parameter from at least one of the 12-leads deviates from a predetermined threshold.

The processor configured to process the one or more ECG acquisition device data and to generate an output based on the processed data may reside in an interactive skin device positioned in or proximate to the skin of the human. The interactive skin device may include a flexible display layer 22. a cover layer 26, and a control circuit configured to control operation of the flexible display layer.

The interactive device may trigger an alert when the at least one monitored physical parameter deviates from a predetermined threshold.

The interactive skin device may include a touch sensitive layer 24 and the control circuit may be configured to control operation of touch sensitive elements.

The cover layer may include a transparent display cover layer 26.

The proximate positioning of the interactive device may be below the epidermis of the human.

The interactive skin device may include an encapsulation layer comprising a biocompatible material. The encapsulation layer may be configured to seal the interactive skin device so as to isolate inner components of the interactive skin device from the environment of the living thing The alert may include a transdermal visual display, an auditory display, and so on.

The visual display rendered on the flexible display layer may be projected through and rendered on the epidermis.

The cover layer may include at least one raised pattern that may be recognized through the epidermis on touch. The at least one raised pattern may be associated with at least one function of the interactive skin device. The touch of the at least one raised pattern may activate the at least one function.

The proximate positioning of the interactive device may be outside the epidermis.

The interactive skin device may include a supporting layer and a sleeve, the supporting layer being disposed between the interactive skin device and the sleeve, the interactive skin device being adapted to a portion of the sleeve; and the sleeve being disposed about a portion of a body of the human.

In another aspect, the one or more ECG acquisition devices may include a first ECG acquisition device, a second ECG acquisition device, a third ECG acquisition device, a fourth ECG acquisition device, and a fifth ECG acquisition device. The first ECG acquisition device may include a first implanted electrode being implantably positioned on a right arm below an outside surface of epidermis of the skin of a human and in electrical communication with a first processor, memory, and a communication circuit. The second ECG acquisition device may include a second implanted electrode being implantably positioned on a left arm below an outside surface of epidermis of the skin of a human and in electrical communication with a second processor, memory, and a communication circuit. The third ECG acquisition device may include a third implanted electrode being implantably positioned on a left leg below an outside surface of epidermis of the skin of a human and in electrical communication with a third processor, memory, and a communication circuit. The fourth ECG acquisition device may include a fourth implanted electrode being implantably positioned on a right leg below an outside surface of epidermis of the skin of a human and in electrical communication with a fourth processor, memory, and a communication circuit. The fifth ECG acquisition device may include a fifth implanted electrode being implantably positioned as a precordial lead V1 at the 4th intercostal space on the right side of the sternum, a sixth implanted electrode being implantably positioned as a precordial lead V2 at the 4th intercostal space on the left side of the sternum a seventh implanted electrode being implantably positioned as a precordial lead V3 at the 5th intercostal space midway between V4 and V2, an eighth implanted electrode being implantably positioned as a precordial lead V4 at the 5th intercostal space midclavicular, a ninth implanted electrode being implantably positioned as a precordial lead V5 at the 5th intercostal space midway between V4 and V6, a tenth implanted electrode being implantably positioned as a precordial lead V6 at the 5th intercostal space midaxillary. The fourth, fifth, sixth, seventh, eighth, ninth, and tenth implanted electrodes device may be in electrical communication with a fifth processor, memory, and a communication circuit of the fourth fifth ECG acquisition device. The first ECG acquisition device, the second ECG acquisition device, the third ECG acquisition device, the fourth ECG acquisition device, and the fifth ECG acquisition device may be in electrical communication with the processor configured to process the ECG acquisition device data and to generate an output based on the processed data. The ten electrodes may form a 12-lead electrocardiogram. The processor configured to process the one or more ECG acquisition device data and to generate an output based on the processed data may trigger an alert when a physical parameter from at least one of the 12-leads deviates from a predetermined threshold.

In another aspect, the one or more ECG acquisition devices may include three implanted electrodes in electrical communication with the processor configured to process the ECG acquisition device data and to generate an output based on the processed data. A first of the three implanted electrodes device may be implantably positioned on a right arm below an outside surface of epidermis of the skin of a human. A second of the three implanted electrodes may be implantably positioned on a left arm below an outside surface of epidermis of the skin of a human. A third of the three implanted electrodes may be implantably positioned on a left leg below an outside surface of epidermis of the skin of a human. The three electrodes may form a 3-lead electrocardiogram. The processor configured to process the one or more ECG acquisition device data and to generate an output based on the processed data may trigger an alert when a physical parameter from at least one of the 3-leads deviates from a predetermined threshold.

The electrocardiographic data monitoring system may further include a fourth electrode implantably positioned on a right leg below an outside surface of epidermis of the skin of a human and in electrical communication with the processor configured to process the ECG acquisition device data and to generate an output based on the processed data. The four electrodes may form a 4-lead electrocardiogram. The processor configured to process the one or more ECG acquisition device data and to generate an output based on the processed data may trigger an alert when a physical parameter from at least one of the 4-leads deviates from a predetermined threshold.

In another aspect, an electrocardiographic data monitoring system may include one implanted electrode in electrical communication with the processor configured to process the ECG acquisition device data and to generate an output based on the processed data. The implanted electrode may be positioned on an arm below an outside surface of epidermis of the skin of a human. The one electrode may form a 1-lead electrocardiogram. The processor configured to process the one or more ECG acquisition device data and to generate an output based on the processed data may trigger an alert when a physical parameter from at least one of the 1-lead deviates from a predetermined threshold.

The arm may be a left arm.

In another aspect is a method for monitoring physical parameters of a living thing. The method may include positioning an interactive skin device in or proximate to the epidermis of the living thing; monitoring by the interactive skin device of at least one physical parameter generated by an implanted medical device; and triggering an alarm when the at least one monitored physical parameter deviates from a predetermined threshold.

The method may further include providing data on the at least one monitored physical parameter.

The method may include providing data on the at least one monitored physical parameter on touch input of the interactive skin device.

The method may include communicating data on the at least one monitored physical parameter to an external device.

The method may include proximally positioning the interactive skin device below the epidermis of the living thing.

The method may include proximally positioning the interactive skin device outside the epidermis of the living thing.

The method may include sealing the interactive skin device inside the epidermis of the living thing with a biocompatible material.

The method may include comprising projecting a visual display from the interactive skin device through the epidermis.

The method may further include rendering a visual display projected from the interactive skin on the epidermis.

Some illustrative claims include:

1. An interactive skin device positioned in or proximate to the skin of a living thing, the interactive skin device monitoring at least one physical parameter generated by an implanted medical device, the interactive device comprising;
    a flexible display layer;
    a cover layer; and
    a control circuit, the control circuit configured to control operation of the flexible display layer;
wherein the interactive skin device triggers an alert when the at least one monitored physical parameter deviates from a predetermined threshold.

2. The interactive skin device of claim 1, the interactive skin device further comprising a touch sensitive layer and the control circuit being configured to control operation of touch sensitive elements.

3. The interactive skin device of claim 1, wherein the cover layer comprises a transparent display cover layer 26.

4. The interactive skin device of claim 2 wherein the living thing is a human.

5. The interactive skin device of claim 2 wherein the living thing is an animal.

6. The interactive skin device of claim 2 wherein the interactive skin provides data on the at least one monitored physical parameter.

7. The interactive skin device of claim 2 wherein the interactive skin provides data on the at least one monitored physical parameter on touch input of the interactive skin device.

8. The interactive skin device of claim 1 or 2 further comprising a communication circuit, the communication circuit being configured to communicate with an external computing device.

9. The interactive skin device of claim 1 or 2, further comprising a communication circuit, the communication circuit being configured to be in electrical communication with the implanted medical device.

10. The interactive skin device of claim 8 wherein the external computing device is selected from the group consisting of a smart phone, portable computer, personal computer, and server computer.

11. The interactive skin device of claim 9 wherein the communication circuitry is selected from the group consisting of wireless, wired, and optical communication circuitry.

12. The interactive skin device of claim 1 wherein the proximate positioning of the interactive device is in proximate to the epidermis of the living thing.

13. The interactive skin device of claim 12, the implanted interactive skin device further comprising an encapsulation layer comprising a biocompatible material, the encapsulation layer configured to seal the interactive skin device so as to isolate inner components of the interactive skin device from the environment of the living thing.

14. The interactive skin device of claim 12 wherein the alert is selected from the group consisting of a transdermal visual display and an auditory display.

15. [The interactive skin device of claim 14 wherein the visual display rendered on the flexible display layer being projected through the epidermis.

16. The interactive skin device of claim 1 wherein the cover layer comprises at least one raised pattern that may be recognized through the epidermis on touch; wherein the at least one raised pattern being associated with at least one function of the interactive skin device; wherein touch of the at least one raised pattern activates the at least one function.

17. The interactive skin device of claim 4 wherein the proximate positioning of the interactive device is outside the epidermis of the human.

18. The interactive skin device of claim 17 further comprising an interactive skin device supporting layer disposed between the interactive skin device and the epidermis.

19. The interactive skin device of claim 18 wherein the interactive skin device supporting layer is an adhesive; the adhesive being adapted to a portion of the epidermis, the interactive skin device being adapted to a portion of the adhesive.

20. The interactive skin of claim 19 wherein the adhesive is an epidermal adhesive.

21. The interactive skin device of claim 17 further comprising an interactive skin device supporting member configured to hold the interactive skin device in a spatial relationship with respect to the epidermis.

22. The interactive skin device of claim 21 wherein the interactive skin device supporting member comprises one or more connectors configured for attaching the interactive skin device to the human.

23. The interactive skin device of claim 22 wherein the one or more connectors comprise one or more adhesive spots disposed on the epidermis configured for attaching the interactive skin device to the human when the interactive skin device is placed against the one or more adhesive spots.

24. The interactive skin device of claim 22 wherein the one or more connectors are surgical stitches.

25. The interactive skin device of claim 22 wherein the one or more connectors are surgically attached to the body.

26. The interactive skin device of claim 25 wherein the one or more connectors are one of a pair of a Velcro hook and loop fastener surgically attached to the human, an other of the pair of a Velcro hook and loop fastener being attached to the interactive skin device, and the engagement of the one and the other of the pair of a Velcro hook and loop fastener being the attachment of the interactive skin device to the human.

27. The interactive skin device of claim 18 wherein the interactive skin device supporting layer disposed between the interactive skin device and the epidermis is a sleeve configured to be worn about a portion of the body of the human; the interactive skin device being adapted to a portion of the sleeve.

28. The interactive skin device of claim 27 wherein the sleeve comprises a biocompatible material.

29. The interactive skin device of claim 27 wherein the interactive skin device is adapted to a ventral portion of the sleeve and the sleeve is disposed about a forearm of the human.

30. The interactive skin device of claim 27 wherein the interactive skin device being adapted to a supporting member configured to hold the interactive skin device in a spatial relationship to the sleeve.

31. The interactive skin device of claim 30 wherein the interactive skin device to sleeve supporting member comprises one or more connectors configured for attaching the interactive skin device to the sleeve.

32. The interactive skin device of claim 31 wherein the one or more connectors are one of a pair of a Velcro hook and loop fastener surgically attached to the sleeve, another of the pair of a Velcro hook and loop fastener being attached to the interactive skin device, and the engagement of the one and the other of the pair of a Velcro hook and loop fastener being the attachment of the interactive skin device to the sleeve.

33. The interactive skin device of claim 31 wherein the one or more connectors are stitches.

34. The interactive skin device of claim 27 wherein the interactive skin device is adapted to a ventral portion of the sleeve and the sleeve is disposed about at least a portion of a forearm and upper arm of the human.

35. The interactive skin device of claim 27 wherein the interactive skin device is adapted to a ventral portion of the sleeve and the sleeve is disposed about a thigh of the human.

36. The interactive skin device of claim 12, wherein the implanted interactive skin device further comprises a port selected from the group consisting of an input port and an output port; and wherein the epidermis of the human is provided with an opening configured for enabling an electrical connection between an external wire connector and the port.

37. The interactive skin device of claim 36 wherein the interactive skin device further comprising a sealant layer, the sealant layer being disposed across the port when the port is not being used, the sealant layer configured to seal the implanted interactive skin device so as to protect the human from infection from the opening in the epidermis.

38. The interactive skin device of claim 37 wherein the implanted interactive skin device comprises a member that extends into the epidermis, and wherein the port defined in the implanted interactive skin device opens into the epidermis of the human.

39. The interactive skin device of claim 38, wherein the implanted interactive skin device further comprising a sealant plug, the sealant plug configured to being disposed in the port defined in the implanted interactive skin device when the port is not being used, the sealant plug protecting the human from infection from the opening in the epidermis.

40. The interactive skin device of claim 36 wherein the external wire connector being configured to connect the implanted interactive skin device to an external computing device.

41. The interactive skin device of claim 40 wherein the external computing device is taken from the group consisting of smart phone, portable computer, personal computer, and server computer.

42. The interactive skin device of claim 4 wherein the implanted medical device is selected from a wired or wireless group consisting of a deep brain neurostimulator, a gastric stimulator, a foot drop implant, a cochlear implant, a cardiac defibrillator, a pacemaker, and an insulin pump.

43. The interactive skin device of claim 4 wherein the implanted medical device is selected from a wired or wireless group consisting of one or more orthopedic implants, cardiovascular implants, spinal implants, neurostimulators, ophthalmic implants dental implants, breast implants, facial implants, drug-eluting medical implants, 44. The interactive skin device of claim 4 wherein the implanted medical device is a drug-eluting medical implant, the drug-eluting medical implant selected from the group consisting of drug-eluting vascular stents, drug-eluting wound dressings and protein-eluting scaffolds for tissue regeneration.

45. The interactive skin of claim 13 wherein the one or more biocompatible materials are selected from the group consisting of metallic biomaterials, ceramic biomaterials, polymers biomaterials, natural biomaterials, and glass.

46. The interactive skin device of claim 8; wherein the communication circuitry is selected from the group consisting of wireless, wired, and optical communication circuitry.

47. The interactive skin device of claim 46; wherein the communication between the communication circuit and the external computing device being over a network.

48. An electrocardiographic data monitoring system comprising:
one or more ECG acquisition devices implanted into a human;
a processor configured to receive data from the at least one implanted ECG acquisition device, wherein the processor is configured to process the one or more ECG acquisition device data and to generate an output based on the processed data.

49. The electrocardiographic data monitoring system of claim 48 wherein the one or more ECG acquisition devices comprise ten implanted electrodes in electrical communication with at least one processor, memory, and a communication circuit; a first of the ten implanted electrodes being implantably positioned on a right arm below an outside surface of epidermis of the human, a second of the ten implanted electrodes being implantably positioned on a left arm below an outside surface of epidermis of the human; a third of the ten implanted electrodes being implantably positioned on a left leg below an outside surface of epidermis of the human; a fourth of the ten implanted electrodes being implantably positioned on a right leg below an outside surface of epidermis of the human; a fifth of the ten implanted electrodes being implantably positioned as a precordial lead V1 at the 4th intercostal space on the right side of the sternum below an outside surface of epidermis of the human; a sixth of the ten implanted electrodes being implantably positioned as a precordial lead V2 at the 4th intercostal space on the left side of the sternum below an outside surface of epidermis of the human; a seventh of the ten implanted electrodes being implantably positioned as a precordial lead V3 at the 5th intercostal space midway between V4 and V2 below an outside surface of epidermis of the human; an eighth of the ten implanted electrodes being implantably positioned as a precordial lead V4 at the 5th intercostal space midclavicular below an outside surface of epidermis of the human; a ninth of the ten implanted electrodes being implantably positioned as a precordial lead V5 at the 5th intercostal space midway between V4 and V6 below an outside surface of epidermis of the human; a tenth of the ten implanted electrodes being implantably positioned as a precordial lead V6 at the 5th intercostal space midaxillary below an outside surface of epidermis of the human; wherein the at least one processor of the one or more ECG acquisition devices is in electrical communication with the processor configured to process the one or more ECG acquisition device data and to generate an output based on the processed data; wherein the ten implanted electrodes form a 12-lead electrocardiogram; wherein the processor configured to process the one or more ECG acquisition device data and to generate an output based on the processed data triggers an alert when a physical parameter from at least one of the 12-leads deviates from a predetermined threshold.

50. The electrocardiographic data monitoring system of claim 49 wherein the processor configured to process the one or more ECG acquisition device data and to generate an output based on the processed data resides in an interactive skin device positioned in or proximate to the skin of the human, the interactive skin device comprising;
a flexible display layer 22;
a cover layer 26; and
a control circuit, the circuit configured to control operation of the flexible display layer.

51. The electrocardiographic data monitoring system of claim 50 wherein the interactive device triggers an alert when the at least one monitored physical parameter deviates from a predetermined threshold.

52. The electrocardiographic data monitoring system of claim 50, wherein the interactive skin device further comprising a touch sensitive layer 24 and the control circuit being configured to control operation of touch sensitive elements.

53. electrocardiographic data monitoring system of claim 52, wherein the cover layer comprises a transparent display cover layer 26.

55. The electrocardiographic data monitoring system of claim 50 wherein the proximate positioning of the interactive device is below the epidermis of the human.

56. The electrocardiographic data monitoring system of claim 55, the interactive skin device further comprising an encapsulation layer comprising a biocompatible material, the encapsulation layer configured to seal the interactive skin device so as to isolate inner components of the interactive skin device from the environment of the living thing 57. The electrocardiographic data monitoring system of claim 55 wherein the alert is selected from the group consisting of a transdermal visual display and auditory display.

58. The electrocardiographic data monitoring system of claim 57 wherein the visual display rendered on the flexible display layer being projected through and rendered on the epidermis.

59. The electrocardiographic data monitoring system of claim 55 wherein the cover layer comprises at least one raised pattern that may be recognized through the epidermis on touch; wherein the at least one raised pattern being associated with at least one function of the interactive skin device; wherein touch of the at least one raised pattern activates the at least one function.

60. The electrocardiographic data monitoring system of claim 50 wherein the proximate positioning of the interactive device is outside the epidermis.

61. The electrocardiographic data monitoring system of claim 60 wherein the interactive skin device further comprises a supporting layer and a sleeve, the supporting layer being disposed between the interactive skin device and the sleeve, the interactive skin device being adapted to a portion of the sleeve; and the sleeve being disposed about a portion of a body of the human.

62. The electrocardiographic data monitoring system of claim 48 wherein the one or more ECG acquisition devices comprise a first ECG acquisition device, a second ECG acquisition device, a third ECG acquisition device, a fourth ECG acquisition device, and a fifth ECG acquisition device; wherein the first ECG acquisition device comprises a first implanted electrode being implantably positioned on a right arm below an outside surface of epidermis of the skin of a human and in electrical communication with a first processor, memory, and a communication circuit; wherein the second ECG acquisition device comprises a second implanted electrode being implantably positioned on a left arm below an outside surface of epidermis of the skin of a human and in electrical communication with a second processor, memory, and a communication circuit; wherein the third ECG acquisition device comprises a third implanted electrode being implantably positioned on a left leg below an outside surface of epidermis of the skin of a human in electrical communication with a third processor, memory, and a communication circuit; wherein the fourth ECG acquisition device comprises a fourth implanted electrode being implantably positioned on a right leg below an outside surface of epidermis of the skin of a human and in electrical communication with a fourth processor, memory, and a communication circuit; wherein the fifth ECG acquisition device comprises a fifth implanted electrode being implantably positioned as a precordial lead V1 at the 4th intercostal space on the right side of the sternum, a sixth implanted electrode being implantably positioned as a precordial lead V2 at the 4th intercostal space on the left side of the sternum a seventh implanted electrode being implantably positioned as a precordial lead V3 at the 5th intercostal space midway between V4 and V2, an eighth implanted electrode being implantably positioned as a precordial lead V4 at the 5th intercostal space midclavicular, a ninth implanted electrode being implantably positioned as a precordial lead V5 at the 5th intercostal space midway between V4 and V6, a tenth implanted electrode being implantably positioned as a precordial lead V6 at the 5th intercostal space midaxillary, wherein the fourth, fifth, sixth, seventh, eighth, ninth, and tenth implanted electrodes being in electrical communication with a fifth processor, memory, and a communication circuit of the fourth fifth ECG acquisition device; wherein the first ECG acquisition device, the second ECG acquisition device, the third ECG acquisition device, the fourth ECG acquisition device, and the fifth ECG acquisition device are in electrical communication with the processor configured to process the ECG acquisition device data and to generate an output based on the processed data; wherein the ten electrodes form a 12-lead electrocardiogram; wherein the processor configured to process the one or more ECG acquisition device data and to generate an output based on the processed data triggers an alert when a physical parameter from at least one of the 12-leads deviates from a predetermined threshold.

63. The electrocardiographic data monitoring system of claim 48 wherein the one or more ECG acquisition devices comprise three implanted electrodes in electrical communication with the processor configured to process the ECG acquisition device data and to generate an output based on the processed data; a first of the three implanted electrodes being implantably positioned on a right arm below an outside surface of epidermis of the skin of a human, a second of the three implanted electrodes being implantably positioned on a left arm below an outside surface of epidermis of the skin of a human; a third of the three implanted electrodes being implantably positioned on a left leg below an outside surface of epidermis of the skin of a human; wherein the three electrodes form a 3-lead electrocardiogram; wherein the processor configured to process the one or more ECG acquisition device data and to generate an output based on the processed data triggers an alert when a physical parameter from at least one of the 3-leads deviates from a predetermined threshold.

64. The electrocardiographic data monitoring system of claim 63 further comprising a fourth electrode being implantably positioned on a right leg below an outside surface of epidermis of the skin of a human and in electrical communication with the processor configured to process the ECG acquisition device data and to generate an output based on the processed data; wherein the four electrodes form a 4-lead electrocardiogram; wherein the processor configured to process the one or more ECG acquisition device data and to generate an output based on the processed data triggers an alert when a physical parameter from at least one of the 4-leads deviates from a predetermined threshold.

65. The electrocardiographic data monitoring system of claim 48 wherein the one or more ECG acquisition devices comprises one implanted electrode in electrical communication with the processor configured to process the ECG acquisition device data and to generate an output based on the processed data; the implanted electrode being positioned on an arm below an outside surface of epidermis of the skin of a human; wherein the one electrode forms a 1-lead electrocardiogram; wherein the processor configured to process the one or more ECG acquisition device data and to generate an output based on the processed data triggers an alert when a physical parameter from at least one of the 1-lead deviates from a predetermined threshold.

66. The electrocardiographic data monitoring system of claim 65 wherein the arm is a left arm.

67. A method for monitoring physical parameters of a living thing, the method comprising:
positioning an interactive skin device in or proximate to the epidermis of the living thing;
monitoring by the interactive skin device of at least one physical parameter generated by an implanted medical device; and
triggering an alarm when the at least one monitored physical parameter deviates from a predetermined threshold.

68. The method of claim 67 further comprising providing data on the at least one monitored physical parameter.

69. The interactive skin device of claim 68 further comprising providing data on the at least one monitored physical parameter on touch input of the interactive skin device.

70. The method of claim 67 further comprising communicating data on the at least one monitored physical parameter to an external device.

71. The method of claim 67 further comprising proximally positioning the interactive skin device below the epidermis of the living thing.

72. The method of claim 67 further comprising proximally positioning the interactive skin device outside the epidermis of the living thing.

73. The method of claim 72 further comprising sealing the interactive skin device inside the epidermis of the living thing with a biocompatible material.

74. The method of claim 70 further comprising projecting a visual display from the interactive skin device through the epidermis.

75. The method of claim 70 further comprising rendering a visual display projected from the interactive skin on the epidermis.

The foregoing is merely illustrative of the principles of this invention and various modifications can be made by those skilled in the art without departing from the scope and spirit of the invention.

Various other components may be included and called upon for providing for aspects of the teachings herein. For example, additional materials, combinations of materials, and/or omission of materials may be used to provide for added embodiments that are within the scope of the teachings herein.

While the invention has been described with reference to illustrative embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:
1. A skin implant device, comprising:
a flexible display, the flexible display including a top surface and a bottom surface, the flexible display comprising image pixels;
a touch sensitive material, the touch sensitive material including a top surface and a bottom surface, the touch sensitive material overlaying the top surface of the flexible display;
an implantable encapsulation material, the implantable encapsulation material comprising a material biocompatible with skin;
wherein the implantable encapsulation material encapsulates the flexible display and the touch sensitive material, prevents direct touching of the flexible display and the touch sensitive material by a user when in an implanted environment, and isolates the flexible display and the touch sensitive material from skin when in the implanted environment;
wherein the flexible display renders a display on the image pixels viewable from the top surface of the flexible display through the implantable encapsulation material when in the implanted environment;
wherein the skin implant device can be implanted inside the skin;
wherein the image pixels are programmed to provide brighter lighting to offset the loss of lighting resulting from the projection of light from the image pixels through skin overlaying the top surface of the skin implant device.

2. The skin implant device of claim 1,
wherein the skin implant device further comprises an electrical circuit and an electrical connector port,
wherein the implantable encapsulation material encapsulates the electrical circuit and isolates the electrical circuit from skin when in the implanted environment;
wherein the electrical connector port receives an electrical connector of an electronic component external to the implanted environment;
wherein the electrical connector port extends through the implantable encapsulation material and is configured for connecting the electrical connector to the electrical circuit.

3. The skin implant device of claim 1, comprising;
a control circuit, the control circuit comprising a memory and a processor, the memory including instructions that when executed by the processor cause the processor to:
control an operation of the flexible display; and
render a visual display on the flexible display;
wherein the encapsulation material further encapsulates the control circuit and the encapsulation isolates the control circuit from skin when in the implanted environment.

4. The skin implant of claim 3, wherein the control circuitry activates internet browsing based on data associated with a location and movement of at least one finger of a user with respect to the touch sensitive material without a user directly touching the touch sensitive material.

5. The skin implant of claim 3:
wherein the processor is in communication with a computing device selected from the group consisting of a smart phone, a remote computing device, and a server.

6. The skin implant device of claim 3, further comprising a sensor.

7. The skin implant of claim 3, further comprising a camera.

8. The skin implant device of claim 6, wherein the sensor detects a condition and the skin implant device generates an output in response to the detected condition.

9. The skin implant device of claim 1, wherein the depth of the skin implant device implanted inside the skin is an average depth of 56.6 micron.

10. The skin implant device of claim 1, wherein there is no sensor for quantitatively and qualitatively detecting one or more physiological properties.

11. The skin implant device of claim 2, wherein the electric circuit comprises a control circuit.

12. A skin implant device that renders images from within a recess formed between an outer layer and an inner layer of skin when in an implanted environment, said skin implant device comprising:
a flexible display to be positioned in the recess formed between the outer layer and the inner layer of skin, the flexible display including a top surface and a bottom surface, the flexible display comprising image pixels that renders an image along the top surface of the flexible display when in the implanted environment;
a skin biocompatible material, the skin biocompatible material overlaying the top surface of the flexible display, the skin biocompatible material forming a top surface of the skin implant device;
wherein the skin biocompatible material prevents direct touching of the flexible display by a user when in the implanted environment;
wherein the top surface of the skin implant device being surfaced to contact skin;
wherein the images rendered by the flexible display are projected from the top surface of the flexible display through the top surface of the skin implant device;
wherein the image pixels are programmed to provide brighter lighting to offset the loss of lighting resulting from the projection of light from the image pixels through skin overlaying the top surface of the skin implant device.

13. The skin implant device of claim 12;
wherein a length and width of the flexible display are predetermined such that, when the skin implant device that renders images from a recess formed between an outer layer and an inner layer of skin is in the recess formed between an outer layer and an inner layer of skin in contact with the skin, at least a portion of the top surface of the skin implant device is adapted to skin.

14. The skin implant device of claim 12;
wherein the skin biocompatible material further overlays the bottom surface of the flexible display, the skin biocompatible material forming a bottom surface of the skin implant device;
wherein the bottom surface of the skin implant device being surfaced to contact skin.

15. The skin implant device of claim 12;
wherein a length and width of the flexible display are predetermined such that, when the skin implant device that renders images from a recess formed between an outer layer and an inner layer of skin is in the recess formed between an outer layer and an inner layer of skin in contact with the skin when in the implanted environment, at least a portion of the top surface of the skin implant device promotes the binding of skin to the top surface of the skin implant device at the same time that at least a portion of the bottom surface of the skin implant device is adapted to skin.

16. The skin implant device of claim 12, comprising:
a touch sensitive material, the touch sensitive material being underneath the skin biocompatible material and overlaying the top surface of the flexible display, the touch sensitive material configured to accept touch input, and wherein the touch input renders a display on the image pixels for input and output functions;
a control circuit, the control circuit comprising a memory and a processor, the memory including instructions that when executed by the processor cause the processor to:
control the operation of the flexible display; and
render a visual display on the flexible display.

17. The skin implant device of claim 12,
wherein the skin implant device further comprises an electrical circuit and an electrical connector port;
wherein the implantable encapsulation material encapsulates the electrical circuit and isolates the electrical circuit from skin when in the implanted environment;
wherein the electrical connector port receives an electrical connector of an electronic component external to the implanted environment; and
wherein the electrical connector port extends through the implantable encapsulation material and is configured for connecting the electrical connector to the electrical circuit.

18. The skin implant device of claim 12, in combination with a constellation of implantable ECG acquisition devices.

19. A skin implant device that renders images from within a recess formed between an outer layer and an inner layer of skin when in an implanted environment, said skin implant device comprising:
- a flexible display positioned in the recess formed between the outer layer and the inner layer of skin when in the implanted environment, the flexible display including a top surface and a bottom surface, the flexible display comprising image pixels that renders an image along the top surface of the flexible display when in the implanted environment;
- a skin biocompatible material, the skin biocompatible material overlaying the top surface of the flexible display, the skin biocompatible material forming a top surface of the skin implant device;
- wherein the surface topology of the top surface of the skin implant device is adapted to skin;
- wherein the skin biocompatible material prevents direct touching of the flexible display by a user when in the implanted environment;
- wherein the images rendered by the flexible display are projected from the top surface of the flexible display through the top surface of the skin implant device;
- wherein the image pixels are programmed to provide enhanced brighter lighting to offset the loss of lighting resulting from the projection of light from the image pixels through skin overlaying the top surface of the skin implant device.

20. The skin implant device for rendering images from within a recess formed between an outer layer and an inner layer of skin of claim 19:
- wherein the skin biocompatible material further overlays the bottom surface of the flexible display, the skin biocompatible material forming a bottom surface of the skin implant device;
- wherein the surface topology of the bottom surface of the skin implant device is adapted to skin.

21. The skin implant device of claim 18 that renders images from within a recess formed between an outer layer and an inner layer of skin when in the implanted environment, said skin implant device further comprising:
- a processor, the processor configured to receive data from at least one implanted ECG acquisition device of the constellation of implantable ECG acquisition devices;
- an alert component implanted into a body configured to generate an alert from inside a body;
- a memory coupled to the processor and storing program instructions that when executed by the processor causes the processor to at least:
  - continually or periodically or on demand compare presently generated ECG data from the at least one implanted ECG acquisition device to a predetermined ECG data or data profile to determine any deviation;
  - compare the any determined deviation to medically recommended deviations;
  - cause the processor to trigger an alarm if the comparison shows a deviation outside of the threshold for an alarming condition; and
  - triggering the alarm on the alert component.

22. The skin implant device of claim 21, wherein the alert component is a visual rendering on the flexible display.

23. The skin implant device of claim 21, the skin implant further comprising:
- a speaker; and
- wherein the alert component is an audio transmission on the speaker.

24. The skin implant device of claim 1, in combination with a constellation of implantable ECG acquisition devices.

25. The skin implant device of claim 19, in combination with a constellation of implantable ECG acquisition devices.

* * * * *